(12) United States Patent
Graf

US011235060B2

(10) Patent No.: US 11,235,060 B2
(45) Date of Patent: Feb. 1, 2022

(54) UROGENITAL MEDICAL DEVICE FORMULATION BASED ON SUITABLE BIOCHEMICAL COMPOSITIONS FOR THE STABILIZATION OF THE ACIDITY AND THE REDOX STATE OF THE VAGINAL FLUID

(71) Applicant: PROBIOSWISS AG, Beckenried (CH)

(72) Inventor: Federico Graf, Beckenried (CH)

(73) Assignee: PROBIOSWISS AG, Beckenried (CH)

( * ) Notice: Subject to any disclaimer, the term of this patent is extended or adjusted under 35 U.S.C. 154(b) by 236 days.

(21) Appl. No.: 16/465,208

(22) PCT Filed: Nov. 30, 2017

(86) PCT No.: PCT/IB2017/057547
§ 371 (c)(1),
(2) Date: May 30, 2019

(87) PCT Pub. No.: WO2018/100533
PCT Pub. Date: Jun. 7, 2018

(65) Prior Publication Data
US 2020/0046837 A1     Feb. 13, 2020

(30) Foreign Application Priority Data
Nov. 30, 2016  (WO) ................. PCT/IB2016/057218

(51) Int. Cl.
| | | |
|---|---|---|
| A61K 47/12 | (2006.01) | |
| A61P 31/04 | (2006.01) | |
| A61K 9/00 | (2006.01) | |
| A61P 31/10 | (2006.01) | |
| A61K 9/06 | (2006.01) | |
| A61K 9/48 | (2006.01) | |
| A61K 31/19 | (2006.01) | |
| A61K 35/747 | (2015.01) | |
| A61K 45/06 | (2006.01) | |
| A61K 47/18 | (2017.01) | |
| A61K 47/20 | (2006.01) | |
| A61K 47/26 | (2006.01) | |
| A61K 47/32 | (2006.01) | |
| A61K 47/36 | (2006.01) | |
| A61K 35/00 | (2006.01) | |

(52) U.S. Cl.
CPC ............ *A61K 47/12* (2013.01); *A61K 9/0034* (2013.01); *A61K 9/06* (2013.01); *A61K 9/4858* (2013.01); *A61K 9/4866* (2013.01); *A61K 31/19* (2013.01); *A61K 35/747* (2013.01); *A61K 45/06* (2013.01); *A61K 47/183* (2013.01); *A61K 47/20* (2013.01); *A61K 47/26* (2013.01); *A61K 47/32* (2013.01); *A61K 47/36* (2013.01); *A61P 31/04* (2018.01); *A61P 31/10* (2018.01); *A61K 2035/115* (2013.01)

(58) Field of Classification Search
CPC ...... A61K 9/00; A61K 9/0034; A61K 9/0053; A61K 9/06; A61K 39/00; A61K 39/02; A61K 39/09
USPC ...................... 424/9.1, 9.2, 93.1, 93.2, 93.45
See application file for complete search history.

(56) References Cited

U.S. PATENT DOCUMENTS

| | | | |
|---|---|---|---|
| 5,645,830 A | 7/1997 | Reid et al. | |
| 11,040,076 B2 * | 6/2021 | Graf ..................... | A23L 33/135 |
| 2015/0139969 A1 * | 5/2015 | Nivoliez .............. | A61K 9/0034 |
| | | | 424/93.45 |

FOREIGN PATENT DOCUMENTS

| | | | | |
|---|---|---|---|---|
| EP | 1038951 A1 | 9/2000 | | |
| EP | 1812023 B1 | 8/2012 | | |
| EP | 2561880 B1 | 8/2014 | | |
| EP | 3548045 A1 * | 10/2019 | ............. | A61K 31/19 |
| WO | WO 1997/029763 | 8/1997 | | |
| WO | WO 1998/046261 | 10/1998 | | |
| WO | WO 2005/060937 | 7/2005 | | |
| WO | WO 2006/045474 | 5/2006 | | |
| WO | WO 2009/123982 | 10/2009 | | |
| WO | WO 2010/023222 | 3/2010 | | |
| WO | WO 2016/020861 | 2/2016 | | |

OTHER PUBLICATIONS

EP application No. 17817169.0 Communication dated Feb. 17, 2021 (Year: 2021).*
EP application No. 17817169.0 communication dated Oct. 26, 2021 (Year: 2021).*
Antonio, May A. D., Stephen E. Hawes and Sharon L. Hillier, "The Identification of Vaginal Lactobacillus Species and the Demographic and Microbiologic Characteristics of Women Colonized by These Species", The Journal of Infectious Diseases, vol. 180, Issue 6, Dec. 1999, pp. 1950-1956, https://doi.org/10.1086/315109.
Atassi F., Brassart D., Grob P., Graf F., Servin AL, "Lactobacillus strains isolated from the vaginal microbiota of healthy women inhibit Prevotella bivia and Gardnerella vaginalis in coculture and cell culture", FEMS Immunol Med Microbiol. Dec. 2006;48(3):424-32. Epub Oct. 24, 2006.
Atassi F., Brassart D., Grob P., Graf F., Servin AL., "Vaginal Lactobacillus isolates inhibit uropathogenic *Escherichia coli*", FEMS Microbiol Lett 257 (1): 132-135, 2006.
De Man J.C., Rogosa M., Sharpe M.E., "A medium for the cultivation of lactobacilli", Journal of Applied Bacteriology 23(1): 130-135, 1960.
Donders G.G., Vereecken A, Bosmans E., Dekeersmaecker A, Salembier G., Spitz B, "Definition of a type of abnormal vaginal microbiota that is distinct from bacterial vaginosis: aerobic vaginitis", BJOG. 109(1):34-43, 2002.

(Continued)

*Primary Examiner* — Nita M. Minnifield
(74) *Attorney, Agent, or Firm* — Bryan D. Zerhusen; Nicholas R. Herrel; Cantor Colburn LLP

(57) ABSTRACT

The invention relates to compositions for vaginal or, alternatively, oral administration and to the use of such compositions for stabilizing the vaginal, or, alternatively, the intestinal acidity and establishing favorable conditions for the inhibition of pathogens and the growth of lactobacilli in the urogenital, or, alternatively, gastro-intestinal tract.

23 Claims, 2 Drawing Sheets

(56) References Cited

OTHER PUBLICATIONS

Figure 1:
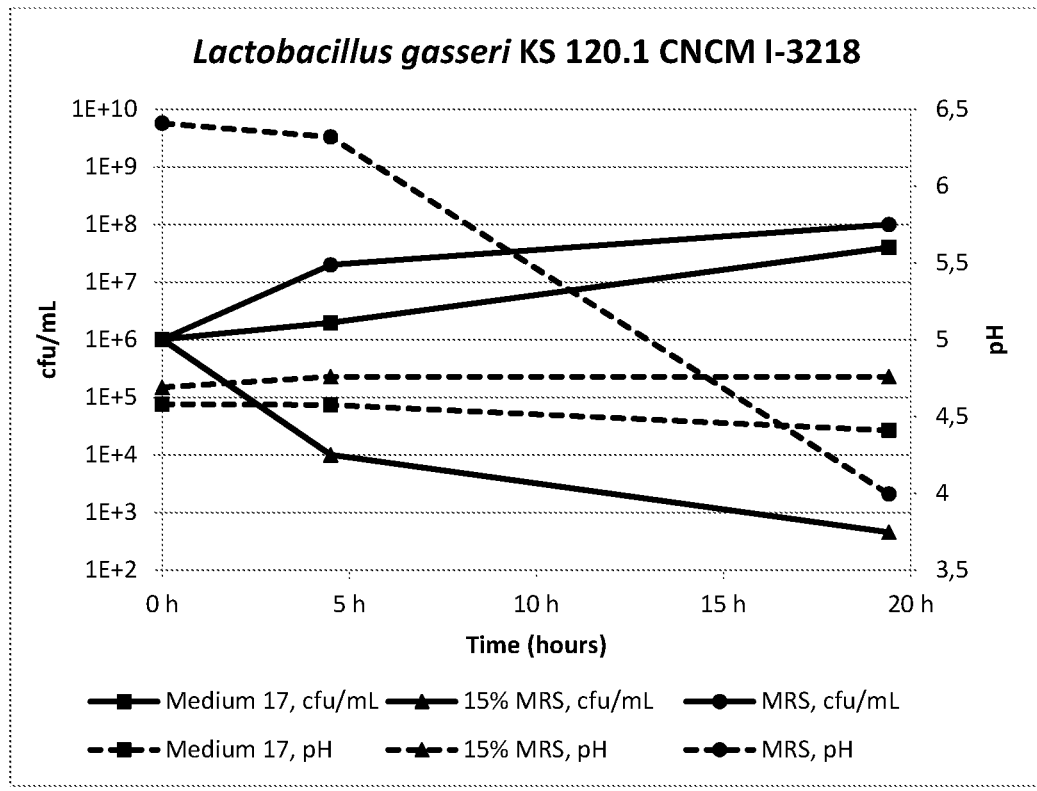

Eschenbach D.A., Thwin S.S., Patton D.L., Hooton T.M., Stapleton AE., Agnew K., Winter C., Amalia Meier A, Walter E. Stamm W.E. 2000, "Influence of the Normal Menstrual Cycle on Vaginal Tissue, Discharge, and Micromicrobiota", Clinical Infectious Diseases 30(6): 901-907, 2000.

Evans DF, Pye G, Bramley R, Clark AG, Dyson TJ, Hardcastle JD, "Measurement of gastrointestinal pH profiles in normal ambulant human subjects", Gut. Aug; 29(8): 1035-41, 1988.

Harding, Mary, et al., http://www.patient.co.uk/doctor/bacterial-vaginosis-pro (May 21, 2015). Up to 70% of patients have a relapse within three months of successful treatment.

Holmes, King K., Kirk C. S. Chen, Carolyn M. Lipinski, David A. Eschenbach, "Vaginal Redox Potential in Bacterial Vaginosis (Nonspecific Vaginitis)", The Journal of Infectious Diseases, vol. 152, Issue 2, Aug. 1985, pp. 379-382, https://doi.org/10.1093/infdis/152.2.379.

Krauss-Silva L., Almada-Horta A., Alves M.B., Camacho K.G., Moreira M.E.L., Braga A., "Basic vaginal pH, bacterial vaginosis and aerobic vaginitis: prevalence in early pregnancy and risk of spontaneous preterm delivery, a prospective study in a low socio-economic and multiethnic South American population". BMC Pregnancy and Childbirth 14:107, 2014.

Laxmi N.P., Mutamed M.A., Nagendra P. S., "Effect of carbon and nitrogen sources on growth of Bifidobacterium animalis BB12 and *Lactobacillus delbrueckii* ssp. *bulgaricus* ATCC 11842 and production of β-galactosidase under different culture condition", International Food Research Journal 18: 373-380, 2011.

Morrison, Douglas J. & Tom Preston, "Gut Microbiota Metabolites in Health and Disease", Gut Microbes vol. 7, Issue 3, Special Issue pp. 189-200, 2016.

Rousseau, V., et al: "Prebiotic effects of oligosaccharides on selected vaginal lactobacilli and pathogenic microorganisms", ANAE, London, GB, vol. 11, No. 3, Jun. 1, 2005 (Jun. 1, 2005), pp. 145-153, XP004807462.

Sawyer, P.R., et al., "Iotrimazole: A Review of its Antifungal Activity and Therapeutic Efficacy", Drugs, vol. 9, Issue 6, pp. 424-447, 1975.

Seib, K.L., et al: "Defenses against Oxidative Stress in Neisseria gonorrhoeae: a System Tailored for a Challenging Environment", Microbiology and Molecular Biology Reviews, vol. 70, No. 2, Jun. 1, 2006 (Jun. 1, 2006), pp. 344-361, XP055447159.

Spurbeck R.R., Arvidson C.G., "Lactobacilli at the front line of defense against vaginally acquired infections", Future Microbiology 6(5): 567-582, 2011.

Srinivasan, Sujatha, et al: "Metabolc Signatures of Bacterial Vaginosis", MBIO, vol. 6, No. 2, Apr. 14, 2015 (Apr. 14, 2015), pp. e00204-e00215, XP055321509.

Vitali, B., et al., "Dynamics of Vaginal Bacterial Communities in Women Developing Bacterial Vaginosis, Candidiasis, or No Infection, Analyzed by PCR-Denaturing Gradient Gel Electrophoresis and Real-Time", Pcrapplied and Environmental Microbiology, Sep. 2007, p. 5731-5741 vol. 73, No. 18.

Vongsa, R.A., et al: "In vitro evaluation of nutrients that selectively confer a competitive advantage to lactobacilli", Beneficial Microbes, vol. 7, No. 2, Mar. 11, 2016 (Mar. 11, 2016), pp. 299-304, XP055391936, NL.

WHO—"Use and procurement of additional lubricants with male and female condoms WHO/UNFPA/FH1360"—Advisory Note, http://apps.who.int/iris/bitstream/10665/76580/1/WHO_RHR_12.33_eng.pdf, WHO (2012).

International Search Report and Written Opinion dated Feb. 16, 2018, for PCT/IB2017/057547.

* cited by examiner

UROGENITAL MEDICAL DEVICE FORMULATION BASED ON SUITABLE BIOCHEMICAL COMPOSITIONS FOR THE STABILIZATION OF THE ACIDITY AND THE REDOX STATE OF THE VAGINAL FLUID

RELATED APPLICATIONS

This application is a National Stage of PCT/IB2017/057547, filed 30 Nov. 2017, titled UROGENITAL MEDICAL DEVICE FORMULATION BASED ON SUITABLE BIOCHEMICAL COMPOSITIONS FOR THE STABILIZATION OF THE ACIDITY AND THE REDOX STATE OF THE VAGINAL FLUID, which claims the benefit and priority to International Patent Application No. PCT/IB2016/057218, filed on 30 Nov. 2016, both of which are incorporated herein by reference in their entirety for all purposes.

FIELD OF THE INVENTION

The invention relates to a biochemical composition of urogenital formulations stabilizing the acidity in the vagina and establishing therein suitable conditions for the inhibition of urogenital pathogens and the growth of lactobacilli. The invention provides compositions for vaginal or, alternatively, oral administration and to the use of such compositions for stabilizing the vaginal, or, alternatively, the intestinal acidity and establishing favorable conditions for the inhibition of pathogens and the growth of lactobacilli in the urogenital, or, alternatively, gastro-intestinal tract. These compositions are based on of chemically defined ingredients, avoiding commonly used natural or ill-defined nutritional components and compositions might be associated with human vaginal strains with specific antimicrobial and/or anti-inflammatory properties.

Furthermore, attention is paid to the proper value of the redox potential following the vaginal administration of such formulation, in particular with respect to the inhibition of bacterial vaginosis (BV)-associated pathogens of the type of *G. vaginalis*.

Finally the formulations are also presented containing an agent to inhibit additionally the growth of opportunistic yeasts such as *Candida albicans* without compromising the growth of lactobacilli.

BACKGROUND TO THE INVENTION

It is well known that useful, well-tolerated non-pathogenic bacteria, the so-called human natural microbiota, predominate in the intestine, the vagina and in the urethra/bladder in the healthy state, whereas the overgrowth of pathogenic and opportunistic microorganisms such as bacteria, yeasts, viruses and protozoa often leads to dysbiosis infections in these organs.

The terms "aerobic bacteria" and "anaerobic bacteria" are commonly used to describe, respectively, those microorganisms requiring air and those unable to grow in the presence of air.

Notably, some of the non-pathogenic and pathogenic bacteria, which can be found in the vagina, can be defined as "non-facultative anaerobe", i.e. they can grow both in the presence and in the absence of air and are basically unaffected by oxidative conditions in the growing medium. Non-limiting examples of such non-facultative anaerobic bacteria are E coil and *Staphylococcus aureus*, which are known to cause a vaginal condition commonly indicated as "aerobic vaginitis".

Other microorganisms which can be found in the vagina are "obligate anaerobes", i.e. they do not grow in the presence of free oxygen and may actually be killed in the presence of oxygen or of oxidative conditions. Anaerobic organisms like *Gardnerella vaginalis*, an obligate anaerobe, migrating from the perineum into the vagina, or acquired through sexual intercourse can cause a dysbiosis with few symptoms, followed by a full blown bacterial vaginosis (BV), which is the most common vaginal infection. BV constitutes a serious risk to premature labor in pregnant women and increases the risk to sexually transmitted infections (Ref. 1). In such cases of vaginal dysbiosis or vaginal infections caused by anaerobes the pH of the vaginal milieu increases from the physiological values of 3.5-4.5 to values reaching 5-6 or even higher. This increase in pH is a critical clinical parameter used in the diagnosis of BV and one of the main cause of the risks associated with BV. The fermentative action of the lactobacilli Döderlein microbiota on the metabolites of glycogen and other carbohydrates present in the vagina and yielding mainly lactic acid as well as other organic acids to a lesser extent and results in the low pH value of vaginal fluids. In addition, certain strains of the Gram-negative *E.coli*, originating from the bowel and migrating first to the vagina and, afterwards to the urethra/bladder are the most common cause of urethritis/cystitis in sexually active women. This same *E.coli* can also cause dysbiosis in the vagina, a condition called aerobic vaginitis, which is also accompanied by a perturbation of the vaginal microbiota, a decrease in vaginal acidity and an increase of the corresponding pH value (Ref. 2).

Another pathogen causing vaginal infections, in particular during pregnancy, is the yeast *Candida* that behaves opportunistically and often co-exists with lactobacilli.

*Candida* is the only yeast organism which behaves as a facultative anaerobe, i.e. it is basically unaffected by the presence or the absence of air and of oxidative conditions.

These infections are usually cured by anti-infective treatment directed against the pathogens that are intended to be successfully eradicated in the course of such therapy, at least to a certain degree. However, in about as much as in 70% of the cases, the patient experiences a relapse or a reinfection within 3 months after a primary treatment (Ref. 3), because either the pathogens were not adequately killed or because of the lack of protection through the restored indigenous vaginal microbiota. This microbiota is actually often damaged as a consequence of the anti-infective therapy. The indigenous vaginal microbiota, historically referred to as Döderlein microbiota, is sensitive to many anti-infective agents and in particular antibiotics. It is often perturbed or even eradicated by the anti-infective therapy and is therefore unable to inhibit the proliferation of the ever present opportunistic, often pathogenic, organisms. As a consequence, a bacterial vaginosis treated by a narrow-spectrum antibiotic specific against anaerobes like clindamycin could lead to a yeast infection, as the *Lactobacillus*-depleted vaginal microbiota can no longer inhibit the opportunistic yeasts.

The possibility of applying exogenous *Lactobacillus* directly to the vagina to treat the dysbiosis or the infection of the vagina had already been suggested by the physician who discovered them, Albert Döderlein himself, in his pioneering book in 1892 (Ref.4). This concept has since then been widely developed in the scientific and patent literature and recently comprehensively reviewed (Ref. 5).

WO 2009/123982 A2 relates to methods and compositions for Lactobacillus replacement therapy, i.e. to colonize vaginal mucosa with a desired microbial species by contacting a vaginal wall with a dried formulation of live microbial cells.

WO 2016/020861 A1 relates to film or sponge compositions, and to a method for the prevention and treatment of vaginal infections, wherein said film or sponge comprises at least a mucoadhesive polumer, at least one probiotic and/or prebiotic and at least one active compound such as an antifungal or antibiotic agent in pharmacologically effective amounts.

In recent years, the inventors prompted thorough investigations about the properties of previously unknown Lactobacillus strains of human vaginal origin relevant to the competition with the most common urogenital pathogens. In particular, the inventors investigated mechanisms involving the interaction of lactic acid, hydrogen peroxide and further agents, which were found to explain the exceptionally strong and specific antibiotic-like activity of, e.g. Lactobacillus gasseri against pathogenic Gardnerella vaginalis and Prevotella bivia (Ref. 6) and the activity of L. jensenii and L. crispatus against uropathogenic E.coli (Ref. 7). The approach as described in the mentioned papers and patents (Ref. 8) has further the advantage of using strains isolated from the same tract of perfectly healthy women for a therapeutic application targeting the urogenital tract. Thereby, possible problems with the tolerability of exogenously administered Lactobacillus strains can be to a large extent reduced in comparison to the use of such strains that are not from human origin and not from the urogenital tract of healthy young women. For strains of non-human origin, the question of the safety and tolerability in therapeutics, e.g., urogenital applications, is not clear a priori and must therefore be assessed a posteriori.

To provide suitable compositions for a pharmaceutically acceptable carrier, the inventors studied the different formulations used in probiotic products and/or described in the literature. In one published approach (Ref. 9) the inventors claim that the use of skim milk resp. skim milk preparations and derivatives called LGF (Lactobacillus growth factor) or NGF (natural growth factor) favors the growth of the desired Lactobacillus by, at the same time, inhibiting the growth of the unwanted uropathogens. Such dedicated growth factors to be used for vaginal applications were also to be found in microbiological growth media, according to the same inventors. The most used such growth medium for Lactobacillus strains is actually the MRS (DeMan-Rogosa-Sharp)-medium (Ref. 10). Besides minerals and vitamins, this broth contains also peptones, sources of carbon and especially nitrogen of chemically ill-defined composition. Other inventors as well recommend the use of complex proteinaceous substances like skim milk and albumin in the preservation matrix of a vaginal medicament containing Lactobacillus strains (Ref. 11).

In our view, while formulations containing natural nutrients such as skim milk or peptones might be useful for special applications, they are not suitable as ingredients in Lactobacillus-containing pharmaceutical formulations for vaginal applications. This is because, first, they are of biological (especially animal) origin, and, second, these natural ingredients have often a chemically ill-defined composition and, thus, they carry an increased risk of causing adverse effects in patients as explained further below. Further, from the point of view of a selective efficacy, these NGF might not achieve the desired effect to inhibit the growth of uropathogens. Not only Lactobacillus strains, but also numerous pathogens can grow in such a rich ingredient (with proteins, carbohydrates, vitamins, minerals, and the like) as skim milk after having been in contact and mixed with the vaginal fluid. Pathogens such as E.coli grow sometimes quicker in milk than in a nutrient broth.

Taking 2 pathogens commonly found in the urogenital microbiota, S. aureus and E. coli, both of which also grow several logs in about 20 hours when inoculated in a medium specific for Lactobacillus such as MRS (Table 1), similar results being obtained also with skim milk (not shown in the following).

TABLE 1

Growth performance of the 2 pathogens in MRS broth.

| Pathogen | Time (h) | $OD_{600\,nm}$ | pH | cfu/ml |
|---|---|---|---|---|
| E. coli CCOS 492 | 0 | 0.05 | 6.5 | Approx. $10^8$ |
|  | 20 | 3.05 | 5.1 | $2.3 \times 10^{10}$ |
| S. aureus CCOS 461 | 0 | 0.05 | 6.5 | Approx. $10^8$ |
|  | 20 | 3.1 | 5.2 | $1.8 \times 10^{10}$ |

Even starting at a relatively high concentration of $10^8$ cfu/ml these pathogens can further grow in MRS by several logs, only to be stopped after about 20 hours in the end by the low pH they generated. That is, a so-called growth medium highly specific for Lactobacillus can also promote the growth of dangerous pathogens. To inhibit the growth of such pathogens, an effective and selective inhibitor has to be added to the formulation.

Therefore, if a subject primarily harbors healthy Lactobacillus strains present in sufficient quantities in the vagina, it might be appropriate to administer L as these indigenous Lactobacillus bacteria can metabolize them. However, it will be inappropriate to administer to a dysbiotic vagina, already infected, or in deficit of beneficial Lactobacillus, LGF of any kind or such unspecific growth factors, as these might boost the growth of the pathogens present instead of that of the rare Lactobacillus strains. A dysbiosis or an infection could even get worse under such treatment with LGF, which risk should be avoided.

In conclusion: skim milk preparations or components of Lactobacillus growth media like MRS might under some circumstances sustain the growth of eubiotic, indigenous vaginal Lactobacillus. However, in general, they are not suitable as therapeutic, ingredients of pharmaceutical formulations to be applied in a dysbiotic vagina, as they have low selectivity for Lactobacillus and are not well-defined chemically. The present invention is intended to overcome these drawbacks.

Owing to the production of lactic and different aliphatic acids by the physiological Döderlein (i.e. vaginal) microbiota vaginal fluids exhibit an acidic pH between 3.5 and 4.5 in average, which appears to be optimum for vaginal homeostasis, as Lactobacillus spp. may still grow at this pH whereby most of the pathogens and opportunistic microbes are inhibited. Above pH 4.5, pathogens can easily grow, however below pH 3.5, the growth of the Döderlein Lactobacillus themselves becomes increasingly inhibited. This acidic vaginal fluid as brought about by the fermentation by the Döderlein microbiota of endogenous carbohydrates like the metabolites of glycogen is the very biochemical foundation of the defense mechanism of the vagina against infections and of primary importance for women's reproductive health (Ref. 12).

Considering these factors, it is not surprising that in the literature, references are found (e.g. Ref. 13) regarding the inclusion of an unspecified pH buffering agent in vaginal composition. In another application (Ref. 14) a composition is recommended that contains a buffering agent (chemically not defined in the mentioned reference) in order to stabilize the acidic degree of the vagina in the range pH 3.5-5.0.

However, the present inventors found that the sole acidic pH is not sufficient to prevent the growth of the pathogens in all cases. Experiments conducted in the inventors' laboratories (shown hereunder) indicate that even below pH 5, relevant pathogens like *S. aureus* and *E.coli* can rapidly grow. The medium used contained lactose as a carbon source and 15% MRS as growth-start promoter.

In conclusion: the importance of the acidic vaginal pH is unchallenged in the scientific community and several authors have recognized the usefulness of adding a buffering agent to a pharmaceutical formulation devised for vaginal application. The pH-range must thereby be clearly defined according to physiology in the range between 3.5 and 4.5. The value of pH 4.5 at the upper limit of the physiological range is deliberately chosen, as it is well tolerated by the patients. More acidic values pH around 4 or lower can cause discomfort such as itching and burning as the vaginal epithelium is more sensitive in cases of dysbiosis and infections.

Furthermore, the buffering agent chemical composition and dosages must be indicated in the pharmaceutical recipe for, e.g., a capsule. Finally, the buffer must be such as to exert its action shortly after the intravaginal administration and to last, at least, until the next administration, i.e. between 12 and 24 hours.

Besides the acidic buffer and the nutrient factors expounded in the above section there are also other factors playing a role in the design of an effective pre- or pro- or symbiotic formulation for vaginal application. One such factor is the redox potential of the vaginal fluid after application of the device.

As we shall show, this is of relevance especially in the case of bacterial vaginosis (BV) where the pathogens are obligate anaerobs (*Gardnerella vaginalis, Prevotella bivia, Atopobium vaginae*, . . . ). The redox potential can indeed influence the growth of these last-mentioned pathogens.

Figure 3:
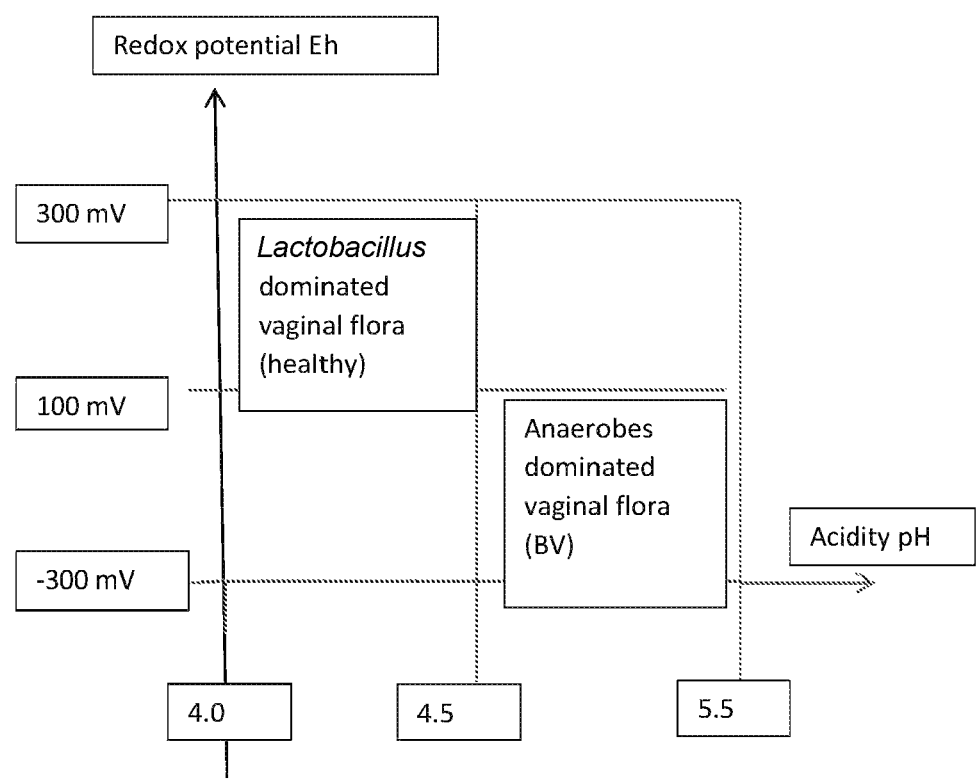

The effect of redox potential on the growth and survival of microrganisms in the vaginal flora is shown in FIG. 3 (according to ref. 22, Eschenbach et al 1985)

Finally, another potentially dangerous microbe is the fungus *Candida albicans*, which is very often present as an opportunist in the vaginal flora. The authors will present a method to control the growth of the fungus without inhibiting that of the vaginal lactobacilli.

The present invention is aimed at providing a solution that addresses these objectives.

SUMMARY OF THE INVENTION

In an embodiment, the present invention relates to a composition for use in the treatment or prevention of urogenital infections caused by pathogenic microorganisms in a female subject, wherein the composition comprises an effective amount of each:
a) a buffering agent,
b) a preservation agent fully compatible with the vaginal microbiota,
c) a pure molecular or ionic biochemical nitrogen-source exploitable by the vaginal microbiota,
d) prebiotic polysaccharide fermentable by the vaginal microbiota,
wherein the treatment or prevention comprises administering the composition intravaginally to the subject, for stabilizing the acidity of the vaginal fluid of a subject at the physiological value around pH 4.5 or lower.

In an embodiment, the present invention provides a method for the treatment or prevention of urogenital infections caused by pathogenic microorganisms in a female subject, which comprises administering intravaginally to the subject, optionally after the anti-infective treatment of a urogenital infection, a formulation with an effective amount of each:
a) a buffering agent,
b) a preservation agent fully compatible with the vaginal microbiota,
c) a pure molecular or ionic biochemical nitrogen-source exploitable by the vaginal microbiota,
d) prebiotic polysaccharide fermentable by the vaginal microbiota,
wherein the treatment or prevention comprises administering the composition intravaginally to the subject.

In another embodiment, the present invention provides a method for stabilizing the acidity of the vaginal fluid of a subject at the physiological value around pH 4.5 or lower, which comprises administering intravaginally to the subject a formulation with an effective amount of each:
a) a buffering agent,
b) a preservation agent fully compatible with the vaginal microbiota,
c) a pure molecular or ionic biochemical nitrogen-source exploitable by the vaginal microbiota,
d) prebiotic polysaccharide fermentable by the vaginal microbiota,
wherein the treatment or prevention comprises administering the composition intravaginally to the subject.

In another embodiment, the present invention relates to a formulation suitable for oral administration having a pH ranging from 4 to 5, wherein the composition comprises an effective amount of each:
a) a buffering agent,
b) a preservation agent fully compatible with the vaginal microbiota,
c) a pure molecular or ionic biochemical nitrogen-source exploitable by the vaginal microbiota,
d) prebiotic polysaccharide fermentable by the vaginal microbiota.

FIGURES

FIG. 1: Graphic representation of the data obtained in growth experiments with *Lactobacillus* gasser/KS 120.1 CNCM I-3218.

Figure 2:
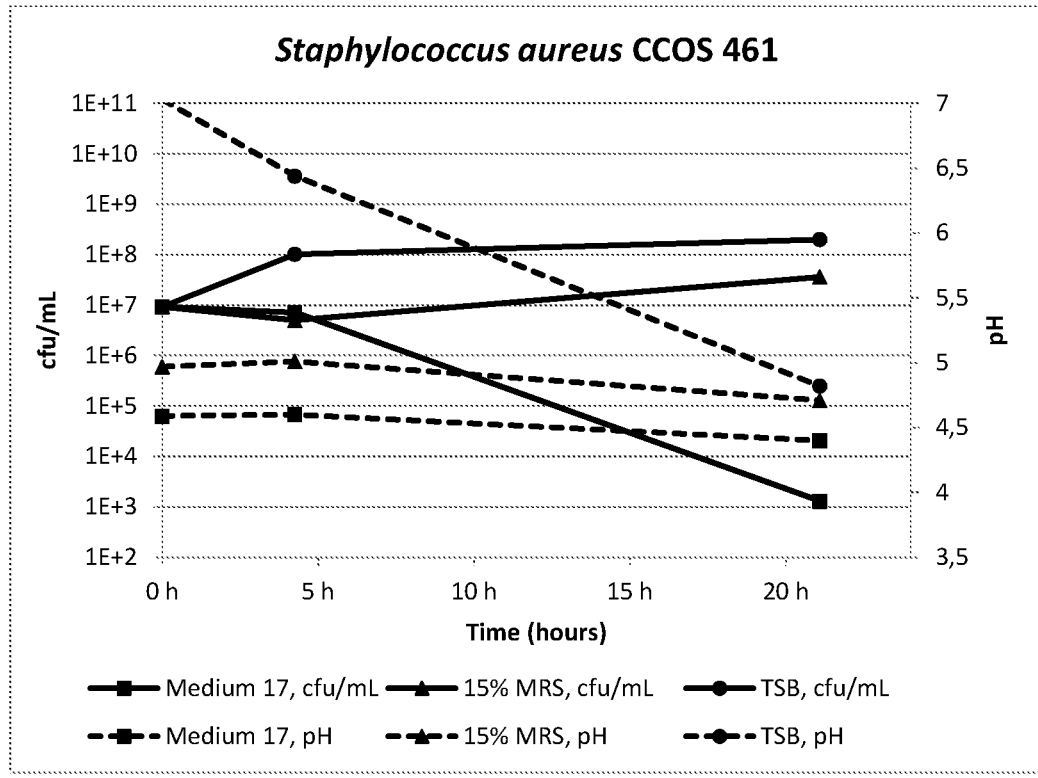

FIG. 2: Graphic representation of the data obtained in growth experiments with multi-resistant *S. aureus* COOS 461.

FIG. 3: Schematic 2-dimensional representation of redox potential Eh and acidity pH in the vagina as a function of the composition of the vaginal microbiota (flora) (according to Ref. Eschenbach et al. 1985)

The present invention provides a composition for use to stabilize the pH of the vaginal fluid at the physiological value around 4.5 and optionally the redox potential of the vaginal fluid above 150 mV for a sufficient duration and to favor selectively the growth of *Lactobacillus* spp, against the growth of pathogens, in particular anaerobes as a method to prevent, mitigate or treat vaginal and urogenital infections such as BV caused by pathogenic micro-organisms, according to the appended claims.

The composition according to the present invention can optionally include a natural, chemically defined substance at a concentration inhibiting *Candida*, but not the *Lactobacillus* bacteria.

ACIDITY AND NUTRIENTS: FORMULATIONS AGAINST FACULTATIVE ANAEROBIC PATHOGENS

This method uses specific, biochemically well-defined compositions of pharmaceutical formulations to be applied vaginally.

The composition in the context of the present invention contains the following biochemical components:

- a biochemical buffering agent to keep the pH of the composition (in vitro and in vivo) in the desired range of 4.0 to 5.0, preferably 4.5, following application and during up to 12-24 h thereafter;
- an anti-pathogenic preservation agent of biochemical nature otherwise fully compatible with the bacterial components of the Döderlein (vaginal) microbiota;
- a biological, chemically defined source of carbon chosen for selectively boosting the growth of *Lactobacillus* spp.;
- a biologically exploitable, otherwise chemically pure source of nitrogen supporting an adequate growth and proliferation of *Lactobacillus* spp. (already present or administered); and optionally
- an adequate, chemically defined sulfur source, assailable by the lactobacilli;
- redox modulators (oxidants in combination with antioxidants in a proper ratio);
- Chemical compounds (organic and/or inorganic) chosen for their specific and targeted anti-infective activity against pathogens of different kinds such as parasites and/or protozoa and/or bacteria and/or fungi and/or viruses and selected minerals, vitamins, and other optional components, which might be relevant for the growth of selected *Lactobacillus* spp. or the inhibition of unwanted pathogens. A non limiting example of antifungal agent, particularly against *Candida*, is sorbate.

Said ingredients can be alone in the composition of the present invention, or else in combination with:

Probiotic *Lactobacillus* strains, as living cells or their lyophilisates, their cell-free culture supernatants or their tyndallisates, selected for their specific properties including, but not limited to, antibiotic-like activity against urogenital pathogens, adhesion to vaginal/urethral epithelial cells, production of $H_2O_2$, lactic acid as well as of relevant bacteriocins and enzymes.

The formulation itself is an appropriate galenic form in a pharmaceutically acceptable carrier or delivery system. The actual composition might be instilled in the form of a freeze-dried preparation, cream, paste, gel liquid or of a suppository, capsule or tablet/stylus for intestinal, urethral or vaginal application. Alternatively, the preparation can be a capsule or tablet or suppository, a cream or gel (lubricant) for vaginal delivery.

The probiotic *Lactobacillus* species named above shall be in the practice of the method administered as viable whole cells, typically in an amount between $10^5$ and $10^{10}$ cfu or as cell free supernatant of the corresponding cultures in liquid, semi-solid or lyophilized form. The *Lactobacillus* species are preferably selected from the group consisting of *L. crispatus, L. jensenii, L. gasseri, L. acidophilus, L. iners, L. plantarum, L. fermentum, L. lactis* and *L. johnsonii*.

On the opposite, the method according to the present invention does not comprise the use of media like natural dairy nutrients or components of animal origin as suggested previously elsewhere. In addition to the fact that the efficacy of said growth factors needs to be further confirmed in clinical studies, such nutrients and components are not suitable for a pharmaceutical intra-vaginal or intra-urethral application for the following medical reasons. They may contain known and unknown substances of proteinaceous nature with allergenic or irritative potential to the sensitive epithelia of vagina and urethra and/or bacterial spores, viruses, prions or components/metabolites thereof that could have survived sterilization and become a potential health threat to the patient.

The same considerations detailed above for the optimal composition of a probiotic formulation apply analogically to the gastro-intestinal (GI) environment. Even though the GI tract is, compared to the urogenital tract, richer in nutrients for the resident microbiota as well as for the pathogens residing there, the concept that the probiotic formulation should help sustaining the optimum acidity and redox state in the GI tract and, at the same time, promoting the growth of healthy probiotic bacteria whilst inhibiting the growth of pathogens and opportunistic species remains valid.

There are, however, two main differences to consider when shifting the focus from the urogenital to the GI tract as an ecosystem.

In first place, the acidity in the GI tract, owing to the nature and length of the same, is variable (Ref. 17). The following pH values are typically measured in normal humans:

a. Stomach: 1.0 to 2.5
b. Proximal small intestine: 6.6
c. Terminal ileum: 7.5
d. Caecum: 6.4
e. Rectum: 7.0

The pH in the intestines varies between 6 and 7, compared to values ranging from 3.5 to 5 in the healthy vagina.

Another difference is that the main acidic fermentation product of the GI microbiota will not be dominantly lactic acid, but a whole range of short chain fatty acids (SCFA), including acetate or butyrate, which constitute the major carbon flux from the diet through the GI microbiota to the host and an important contribution to the host metabolism (Ref. 18).

As a consequence, the prebiotic fibers comprised in the composition according to the invention to improve the metabolism of the strains of the Döderlein microbiota, when applied to the intestine will benefit not only the *Lactobacillus* spp. but also, e.g., the bifidobacteria and other resident species. Advantageously, the composition according to the invention comprises at least two different fibers acting at different levels of the intestine, as the GI microbiota in the upper and in the lower intestine, respectively, is somehow different.

The method according to the invention for the urogenital application can be translated without major change to the oral application. In fact, the optimum pH of an oral preparation containing probiotics is that of the yoghurt or of curdled milk, which is in the region around 4.5 (Ref. 19), the same pH found in the healthy vagina.

For this reason, the considerations developed above, and the experiments performed accordingly retain their validity when considering a suitable oral formulation containing probiotics. As pointed out above the main difference consists in the choice of the prebiotic fibers, as for the intestine it is preferable to include at least two fibers.

As used hereafter, the term "composition" refers to the composition for intravaginal administration as well as to the formulation for oral use, as defined in the attached claims.

The composition according to the present invention may contain the following biochemical components:

a. A biochemical buffering agent to keep the pH of the composition (in vitro and as soon as dissolved in vivo) in the desired range of 4 to 5, preferably 4.5;
b. an anti-pathogenic preservation agent of biochemical nature otherwise fully compatible with the bacterial components of the intestinal lactic acid microbiota;
c. a biologically exploitable, otherwise chemically pure source of nitrogen supporting an adequate growth and proliferation of *Lactobacillus* spp. (already present or administered);
d. biological, chemically defined sources of carbon chosen for selectively boosting the growth of *Lactobacillus* spp. and being fermented in lactic acid as well as SCFA; preferably in combination with
e. a biologically exploitable, otherwise chemically pure source of sulfur supporting an adequate growth and proliferation of *Lactobacillus* spp. (already present or administered);
f. a component modulating the redox potential in the vaginal fluid, which can be comprised in the composition in the presence or in the absence of the sulfur source,
g. selected minerals, and/or vitamins, oxidants/antioxidants and other components that might be relevant for the growth of selected *Lactobacillus* spp, and the inhibition of the pathogens, and
h. Probiotic *Lactobacillus* strains as living cells (or their lyophilisates, their cell-free culture supernatants or their tyndallisates) selected for their specific properties including, but not limited to, antibiotic-like activity against urogenital and/or intestinal pathogens, adhesion to intestinal as well as vaginal/urethral epithelial cells, production of $H_2O_2$, lactic acid as well as of relevant bacteriocins and enzymes.

In the context, of the present invention, the terms "chemically pure" and "chemically defined" indicate a synthetic medium or substance, in which the exact chemical composition is known (ref. Textbook "Basic microbiology" $8^{th}$ edition, W. A: Volk, J. C, Brown, 1997, pages 39-40).

A complex (undefined) medium is one in which the exact chemical constitution of the medium is not known. Defined media are usually composed of pure biochemicals off the shelf; complex media usually contain complex materials of biological origin such as blood or milk or yeast extract or beef extract, the exact chemical composition of which is obviously undetermined. A defined medium is a minimal medium. The formulation itself can be an appropriate galenic formulation in a pharmaceutically acceptable carrier or delivery system. The actual composition in liquid (yoghurt drinks), semisolid (yoghurt, cheese) or solid form, the latter including tablets, capsules, sachets and sticks as well.

The following are preferred embodiments of the invention.

a. Buffering agent

The purpose of such ingredient is to help keeping the pH value of the vaginal liquid after application in the physiological range of pH 4 to 5. Acids and their salts having in solution such desired properties are e.g. organic acids like aliphatic acids: acetic, propionic, butyric a.s.o, acid, dicarboxylic acids like oxalic, malonic, succinic a.s.o. acids, hydroxy-acids like lactic acid, citric acid, dicarboxylic acids like malic acid a.s.o. Also other acids that are found in the human organism can be considered for this use, such as phosphoric acid.

b. anti-pathogenic preservation agent compatible with the Döderlein microbiota

The specificity of the metabolism of lactic acid bacteria is, as the name itself indicates, the production of lactic acid. This is the main reason for the use, in traditional as well as in industrial food preparation, of lactic acid fermentation to kill potential pathogens present in the raw nutrients and to preserve them at the end of the fermentation process through an effective amount of lactic acid (e.g. sauerkraut). As *Lactobacillus* spp., in particular vaginal ones, tolerate well an acidic milieu containing lactic acid, this latter compound is in fact a Döderlein-compatible preservative. Lactic acid respectively selected salts of it (calcium, magnesium, potassium, sodium, ammonium a.s.o) are included in the compositions to reach this effect.

c. biochemically exploitable source of nitrogen to support the growth of *Lactobacillus* spp.

Much attention is presently devoted to the properties and uses of so-called prebiotics, polysaccharides being metabolized specifically by probiotics like lactobacilli and bifidobacteria (see next point). The prebiotics are widely used in combination with probiotic bacteria to yield so-called symbiotics, which, when ingested orally, ensure a better multiplication of the probiotic bacteria in the GI tract. However, in a vaginal environment, the availability of suitable nutrients to the already present or exogenously-administered probiotic bacteria is more limited, in particular with respect to the necessary nitrogen sources (N-sources). The addition of a suitable, organic and/or inorganic, chemically defined and pure N-source in a pharmaceutically suitable carrier appears as an essential factor allowing for a growth and proliferation of *Lactobacillus* spp. in the vagina.

Such chemically defined N-sources are e.g. ammonium salts (e.g. ammonium chloride, Ref. 15), urea, amino acids like glutamic acid and similar (arginine a.s.o.), capable of boosting the growth of lactobacilli and bifidobacteria.

d. biological, chemically defined source of carbon to support the growth of lactobacilli Obviously also a carbon source (C-source) is necessary for the growth of the vaginal lactobacilli. Preferentially, one such source that is a specific nutrient to *Lactobacillus* spp, rather than to opportunistic or pathogenic bacteria. Examples thereof are non-digestible carbohydrates as: fructo-oligosaccharides, galacto-oligosaccharides, glyco-oligosaccharides and others as well. The presence of these so-called prebiotics confers, in the vagina as well as in the intestine, an additional differential competitive advantage for the growth of *Lactobacillus* spp. with respect to that of the present pathogens or opportunists.

Optionally other components are present in the composition according to the invention, such as a sulfur source, minerals, oxidation-reduction (redox) modulators and vitamins.

Preferably, the composition according to the present invention comprises a biologically exploitable, otherwise chemically pure source of sulfur supporting an adequate growth and proliferation of *Lactobacillus* spp, (already present or administered), which may be, without limitation, an organic/inorganic compound such as a sulfate, a sulfite, a sulfide, thiosulphate, a sulfur-containing aminoacid like cysteine and methionine, cysteine (the oxidized dimer of cysteine), a s.o.

Minimal, chemically defined media for the growth of different *Lactobacillus* spp. have been found and published (Ref. 18a). In addition to the components listed above it might be, under circumstances of a very poor availability of nutrients in the vagina, helpful to consider also the addition of the following components to the preferred formulations: metal ions: e.g. $Mg^{2+}$ and $Mn^{2+}$, antioxidants: e.g. vitamin C, N-acetyl cysteine, thiosulphate, vitamins: e.g. riboflavin and nicotinic acid; alone or in combination with each other.

Preferred ingredients are also probiotics as living cells, lyophilisates, tyndallisates, supernatants dried or liquid, of species and strains with proven activity against infectious or inflammatory conditions of the vagina and preferably of human, urogenital origin. Such species can be found in and isolated from the Döderlein microbiota of healthy young women and are worldwide represented by *L. gasseri, L. jensenii, L. crispatus, L. acidophilus, L. fermentum, L. plantarum* and *L. iners*.

Preferred ingredients are also compounds with activity against pathogens (bacteria, viruses, fungi and the like), which, in the intention and understanding of this invention, are those that are typically capable of inhibiting the growth of pathogens without disturbing the metabolism and growth of the probiotic bacteria. Examples of such suitable antifungal compounds of organic or inorganic origin are cysteine, sorbate or thiosulfate, respectively.

Preferably, the composition according to the present invention comprises a biologically exploitable redox modulator, i.e. a component modulating the redox potential in a biological fluid. In the context of the present invention the term "redox modulator" indicates a substance, or at least a pair of substances, capable of reducing or enhancing the redox potential of a certain biological medium. A method for determination of the vaginal redox potential in bacterial vaginosis is indicated in Rf. 22.

Said redox modulator can be comprised in the composition of the presence invention in the presence or in the absence of the sulfur source as above defined.

When the redox modulator is present, the composition according to the present invention is particularly suitable to treat, or to prevent, infections due to obligate anaerobes, e.g. bacterial vaginosis (BV).

Preferably, the redox modulator is chosen among:
sulphur-containing redox systems like sodium thiosulphate/bisulphite and glutathione in the reduced state (GSH) and in the oxidized state (GSSG),
oxygen-based redox systems such as quinone/hydroquinone,
nitrogen-based redox systems such as nitrite/nitrate salts,
selenium-based redox systems (selenite/selenate and selenide). For example, the redox potential can be enhanced so as to become definitely positive (>150 mV, preferably 200-300 mV) and to inhibit anaerobes like *Gardnerella*.

Preferably, in the context of the present invention at least one lactobacilli strain is added to the composition of the invention, said strain being selected from the group consisting of *L. gasseri, L. jensenii, L. crispatus, L. acidophilus, L. helveticus, L. plantarum, L. fermentum* and *L. johnsonii*, more preferably said strain being selected from the group consisting, *L. gasseri* KS 114.1 deposited by Medinova AG at Collection Nationale de Cultures de Microorganismes (CNCM) on Jul. 22, 2005 with accession number CNCM I-3482, *L. crispatus* 116.1 deposited by Medinova AG at Collection Nationale de Cultures de Microorganismes (CNCM) on Jul. 22, 2005 with accession number CNCM I-3483, *L. jensenii* KS 119.1 deposited by Medinova AG at Collection Nationale de Cultures de Microorganismes (CNCM) on Jun. 4, 2004 with accession number CNCM I-3217, *L. crispatus* 119.4 deposited by Medinova AG at Collection Nationale de Cultures de Microorganismes (CNCM) on Jul. 22, 2005 with accession number CNCM I-3484, *L. gasseri* 120.1 deposited by Medinova AG at Collection Nationale de Cultures de Microorganismes (CNCM) on Jun. 4, 2004 with accession number CNCM I-3218, *L. jensenii* KS 121.1 deposited by Medinova AG at Collection Nationale de Cultures de Microorganismes (CNCM) on Jun. 4, 2004 with accession number CNCM I-3219, *L. gasseri* 123.1 deposited by Medinova AG at Collection Nationale de Cultures de Microorganismes (CNCM) on Jul. 22, 2005 with accession number CNCM I-3485, *L gasseri* 126.2, *L. crispatus* 127.1 deposited by Medinova AG at Collection Nationale de Cultures de Microorganismes (CNCM) on Jul. 22, 2005 with accession number CNCM I-3486, and *L. acidophilus* KS 400, most preferably said *Lactobacillus* strain is selected from the group consisting of *L. jensenii* KS 119.1 CNCM I-3217, *L. crispatus* 119.4 CNCM I-3484, *L. gasseri* 120.1 CNCM I-3218, and *L. gasseri* 124.3 CNCM I-3220.

The above indicated bacteria strains have been deposited under the conditions of the Budapest Treaty and are made available to the public.

Preferably, in the context of the present invention the buffering agent a) is an acid, or a salt thereof, selected from the groups comprising, or, alternatively, consisting of organic acids such as aliphatic acids, including acetic, propionic, butyric acid, dicarboxylic acids including oxalic, malonic, succinic acid, hydroxy-acids like lactic acid, citric acid, dicarboxylic acids like malic acid.

Preferably, in the context of the present invention the preservation agent b) is lactic acid, or a derivative and/or salt thereof.

Preferably, in the context of the present invention the source of nitrogen c) is an ammonium salt, urea, a naturally-occurring or synthetic amino acid such as glutamic acid, and mixtures thereof.

Preferably, in the context of the present invention the source of carbon d) is a non-digestible carbohydrate such as: fructo-oligosaccharides, galacto-oligosaccharides, glyco-oligosaccharides and mixtures thereof.

Preferably, the composition according to the present invention comprises e.g. the following ingredients based on 1 ml of solution/suspension of the ingredients. The actual composition of e.g. a tablet or capsule is obtained by multiplying the quantity of ingredients by 3:

| Final pH of solution/suspension: approx. 4.5 | *Lactobacillus*-compatible Preservation agent | Ca-lactate pentahydrate | 10-30, preferably 20 mg/ml |
|---|---|---|---|
| | Buffer system | Dibasic magnesium citrate | 5-15, preferably 10 mg/ml |
| | Carbon source | α-Glyco-oligosaccharide | 15-30, preferably 20 mg/ml |
| | Nitrogen source | Glutamic acid | 10-30 mg |
| | Sulfur source | cystine | 10-30 mg |
| | | Excipients q.s. | 150-250 mg |

The invention comprises the following embodiments (E).

E1. A composition for use in the treatment or prevention of urogenital infections caused by pathogenic microorganisms in a female subject, the subjects wherein the composition comprises an effective amount of each:
a) a buffering agent,
b) a preservation agent fully compatible with the vaginal microbiota, c) a pure molecular or ionic biochemical nitrogen-source exploitable by the vaginal microbiota,
d) prebiotic polysaccharide fermentable by the vaginal microbiota, and, optionally,
e) an antioxidant component,
wherein the treatment or prevention comprises administering the composition intravaginally to the subject, for stabilizing the acidity of the vaginal fluid of a subject at the physiological value around pH 4.5 or lower.

E2. The composition for use according to E1, wherein the vaginal formulation is a lubricant gel for personal use.

E3. The composition for use according to E1 or E2, wherein the antioxidant is chosen among sulphur-containing compounds like N-acetyl cysteine, cysteine, methionine, sodium thiosulphate.

E4. The composition for use according to any one of E1-E3, wherein one or more lactobacilli strains are added to the formulation from the group consisting of *L. gasseri, L. jensenii, L. crispatus, L. acidophilus, L. helveticus, L. plantarum, L. fermentum, L. lactis, L. johnsonii* and *L. acidophilus* KS 400.

E5. The composition for use according to any one of E1-E4, wherein one or more lactobacilli strains are added to the formulation from the group consisting of *L. gasseri, L. jensenii, L. crispatus, L. acidophilus, L. helveticus, L. plantarum. L. fermentum, L. lactis* and *L. johnsonii*.

E6. The composition for use according to any one of E1-E5, in said *Lactobacillus* strain are selected from the group consisting of *L. jensenii* KS 109, *L. gasseri* KS 114.1 deposited by Medinova AG at Collection Nationale de Cultures de Microorganismes on Jul. 22, 2005 with accession number CNCM I-3482, *L. crispatus* 116.1 deposited by Medinova AG at Collection Nationale de Cultures de Microorganismes (CNCM) on Jul. 22, 2005 with accession number CNCM I-3483, *L. jensenii* KS 119.1 deposited by Medinova AG at Collection Nationale de Cultures de Microorganismes (CNCM) on Jun. 4, 2004 with accession number CNCM I-3217, *L. crispatus* 119.4 deposited by Medinova AG at Collection Nationale de Cultures de Microorganismes (CNCM) on Jul. 22, 2005 with accession number CNCM I-3484, L gasser/120.1 deposited by Medinova AG at Collection Nationale de Cultures de Microorganismes (CNCM) on Jun. 4, 2004 with accession number CNCM I-3218, *L. jensenii* KS 121.1 deposited by Medinova AG at Collection Nationale de Cultures de Microorganismes (CNCM) on Jun. 4, 2004 with accession number CNCM I-3219, *L. jensenii* KS 122.1, *L gasseri* 123.1 deposited by Medinova AG at Collection Nationale de Cultures de Microorganismes (CNCM) on Jul. 22, 2005 with accession number CNCM I-3485, *L gasseri* 124.3 deposited by Medinova AG at Collection Nationale de Cultures de Microorganismes (CNCM) on Jun. 4, 2004 with accession number CNCM I-3220, *L gasseri* 126.2, *L crispatus* 127.1 deposited by Medinova AG at Collection Nationale de Cultures de Microorganismes (CNCM) on Jul. 22, 2005 with accession number CNCM I-3486, *L. jensenii* KS 130.1, *L. helveticus* KS 300 deposited by Medinova AG at Collection Nationale de Cultures de Microorganismes (CNCM) on Feb. 10, 2005 with accession number CNCM I-3360 and *L. acidophilus* KS 400.

E7. The composition for use according to any one of E1-E6, wherein said *Lactobacillus* strain is selected from the group consisting of *L. jensenii* KS 119.1 deposited by Medinova AG at Collection Nationale de Cultures de Microorganismes (CNCM) on Jun. 4, 2004 with accession number CNCM I-3217, *L crispatus* 119.4 deposited by Medinova AG at Collection Nationale de Cultures de Microorganismes (CNCM) on Jul. 22, 2005 with accession number CNCM I-3484, *L. gasseri* 120.1 deposited by Medinova AG at Collection Nationale de Cultures de Microorganismes (CNCM) on Jun. 4, 2004 with accession number CNCM I-3218, *L. gasseri* 124.3 deposited by Medinova AG at Collection Nationale de Cultures de Microorganismes (CNCM) on Jun. 4, 2004 with accession number CNCM I-3220.

E8. The composition for use according to any one of E1-E7, wherein the formulation further comprises an effective amount of a therapeutically effective antimicrobial agent capable to inhibit or eradicate the urogenital pathogens.

E9. A method for the treatment or prevention of urogenital infections caused by pathogenic microorganisms in a female subject, which comprises administering intravaginally to the subject, optionally after the anti-infective treatment of a urogenital infection, a formulation with an effective amount of each:
a) a buffering agent,
b) a preservation agent fully compatible with the vaginal microbiota,
c) a pure molecular or ionic biochemical nitrogen-source exploitable by the vaginal microbiota,
d) prebiotic polysaccharide fermentable by the vaginal microbiota, and, optionally,
e) an antioxidant component.

E10. A method for stabilizing the acidity of the vaginal fluid of a subject at the physiological value around pH 4.5 or lower, which comprises administering intravaginally to the subject a formulation with an effective amount of each:
a) a buffering agent,
b) a preservation agent fully compatible with the vaginal microbiota,
c) a pure molecular or ionic biochemical nitrogen-source exploitable by the vaginal microbiota,
d) prebiotic polysaccharide fermentable by the vaginal microbiota, and, optionally,
e) an antioxidant component.

E11. The method according to claim 9 or 10, wherein the buffering agent a) is an acid, or a salt thereof, selected from the groups comprising, or, alternatively, consisting of organic acids such as aliphatic acids, including acetic, propionic, butyric acid, dicarboxylic acids including oxalic, malonic, succinic acid, hydroxy-acids like lactic acid, citric acid, dicarboxylic acids like malic acid.

E12. The method according to any one of E9-E11, wherein the preservation agent b) is lactic acid, or a derivative and/or salt thereof.

E13. The method according to E9-E12 wherein the source of nitrogen c) is an ammonium salt, urea, a naturally-occurring or synthetic amino acid such as glutamic acid, and mixtures thereof.

E14. The method according to any one of claims E9-E13, wherein the source of carbon d) is a non-digestible carbohydrate such as: fructo-oligosaccharides, galacto-oligosaccharides, glyco-oligosaccharides and mixtures thereof.

E15. A formulation suitable for oral administration having a pH ranging from 4 to 5, wherein the composition comprises an effective amount of each:

a) a buffering agent,
b) a preservation agent fully compatible with the gastrointestinal microbiota,
c) a pure molecular or ionic biochemical nitrogen-source,
d) prebiotic polysaccharide fermentable by the gastrointestinal microbiota, and, optionally,
e) an antioxidant component.

E16. The formulation of claim E15, wherein the antioxidant e) is chosen among sulphur-containing compounds like N-acetyl cysteine, cysteine, methionine, sodium thiosulphate.

E17. The formulation of claim E15 or E16, wherein at least one lactobacilli strain is added to the formulation, said strain being selected from the group consisting of *L. gasseri, L. jensenii, L. crispatus, L acidophilus L. helveticus, L. plantarum, L fermentum* and *L. johnsonii*.

E18. The formulation of any one of E15 to E17, wherein at least one lactobacilli strain is added to the formulation, said strain being selected from the group consisting of *L. jensenii* KS 109, *L gasseri* KS 114.1 deposited by Medinova AG at Collection Nationale de Cultures de Microorganismes on Jul. 22, 2005 with accession number CNCM I-3482, *L crispatus* 116.1 deposited by Medinova AG at Collection Nationale de Cultures de Microorganismes (CNCM) on Jul. 22, 2005 with accession number CNCM I-3483, *L. jensenii* KS 119.1 deposited by Medinova AG at Collection Nationale de Cultures de Microorganismes (CNCM) on Jun. 4, 2004 with accession number CNCM I-3217, *L. crispatus* 119.4 deposited by Medinova AG at Collection Nationale de Cultures de Microorganismes (CNCM) on Jul. 22, 2005 with accession number CNCM I-3484, *L. gasseri* 120.1 deposited by Medinova AG at Collection Nationale de Cultures de Microorganismes (CNCM) on Jun. 4, 2004 with accession number CNCM I-3218, *L. jensenii* KS 121.1 deposited by Medinova AG at Collection Nationale de Cultures de Microorganismes (CNCM) on Jun. 4, 2004 with accession number CNCM I-3219, *L. jensenii* KS 122.1, *L. gasseri* 123.1 deposited by Medinova AG at Collection Nationale de Cultures de Microorganismes (CNCM) on Jul. 22, 2005 with accession number CNCM I-3485, *L. gasseri* 124.3 deposited by Medinova AG at Collection Nationale de Cultures de Microorganismes (CNCM) on Jun. 4, 2004 with accession number CNCM I-3220, *L. gasseri* 126.2, *L. crispatus* 127.1 deposited by Medinova AG at Collection Nationale de Cultures de Microorganismes (CNCM) on Jul. 22, 2005 with accession number CNCM I-3486, *L. jensenii* KS 130.1, *L. helveticus* KS 300 deposited by Medinova AG at Collection Nationale de Cultures de Microorganismes (CNCM) on Feb. 10, 2005 with accession number CNCM I-3360 and *L. acidophilus* KS 400.

E19. The formulation of any one of E15 to E18 wherein said *Lactobacillus* strain are selected from the group consisting *L. jensenii* KS 119.1 deposited by Medinova AG at Collection Nationale de Cultures de Microorganismes (CNCM) on Jun. 4, 2004 with accession number CNCM I-3217, *L. crispatus* 119.4 deposited by Medinova AG at Collection Nationale de Cultures de Microorganismes (CNCM) on Jul. 22, 2005 with accession number CNCM I-3484, *L. gasseri* 120.1 deposited by Medinova AG at Collection Nationale de Cultures de Microorganismes (CNCM) on Jun. 4, 2004 with accession number CNCM I-3218, *L. gasseri* 124.3 deposited by Medinova AG at Collection Nationale de Cultures de Microorganismes (CNCM) on Jun. 4, 2004 with accession number CNCM I-3220 and *L. acidophilus* KS 400.

E20. The composition for use according to any one of E1-E8, or formulation according to any one of E15-E19, wherein the buffering agent a) is an acid, or a salt thereof, selected from the groups comprising, or, alternatively, consisting of organic acids such as aliphatic acids, including acetic, propionic, butyric acid, dicarboxylic acids including oxalic, malonic, succinic acid, hydroxy-acids like lactic acid, citric acid, dicarboxylic acids like mate acid.

E21. The composition for use according to any one of E1-E8 or E20, or formulation according to any one of claims 15-20, wherein the preservation agent b) is lactic acid, or a derivative and/or salt thereof.

E22. The composition for use according to any one of E1-E8 or E20-E21, or formulation according to any one of claims 15-21, wherein the source of nitrogen c) is an ammonium salt, urea, a naturally-occurring or synthetic amino acid such as glutamic acid, and mixtures thereof.

E23. The composition for use according to any one of E1-E8 or E20-E22, or formulation according to any one of E15-E22, wherein the source of carbon d) is a non-digestible carbohydrate such as: fructo-oligosaccharides, galacto-oligosaccharides, glyco-oligosaccharides and mixtures thereof.

E24. The composition for use according to any one of E1-E8 or E20-E23, or formulation according to any one of claims 15-23, having pH from 4.3 to 4.6, if solid after dissolution/suspension to a volume of 3 ml, and which comprises the following ingredients per single dosage:

Ca-lactate pentahydrate: 30-90, preferably 60 mg
Dibasic magnesium citrate: 15-45, preferably 30 mg
Prebiotic fibre: 50-150, preferably 100 mg
Glutamic acid: 20-60, preferably 40 mg
Cystein/Thiosulphate: 10-50, preferably 30 mg
Excipients ad 400-1100 mg: q.s.

E25. The composition for use or formulation according to E24, further comprising:

Lyophilisates of *L. gasseri* 120.1 deposited by Medinova AG at Collection Nationale de Cultures de Microorganismes (CNCM) on Jun. 4, 2004 with accession number CNCM I-3218 and/or

*L. gasseri* 124.3 and/or *L. crispatus* 119.4 deposited by Medinova AG at Collection Nationale de Cultures de Microorganismes (CNCM) on Jul. 22, 2005 with accession number CNCM I-3484 and/or

*L. jensenii* KS 119.1 deposited by Medinova AG at Collection Nationale de Cultures de Microorganismes (CNCM) on Jun. 4, 2004 with accession number CNCM I-3217 for a total of 2 to 10 billion c.f.u. amounting to 50 to 200 mg.

EXAMPLES

Example 1

Composition of Different Growth Media and Conditions of Growth

Assuming a complete dissolution in the vaginal milieu (volume: 2-5 ml) a number of compositions are presented to allow for a comparative growth of *Lactobacillus* spp. and pathogens under test conditions:

Growth control (positive) for lactobacilli: MRS

The conventional MRS medium (Biolife) without pH-adjustment allows for optimum growth of *Lactobacillus* spp. and is chosen for this purpose.

Growth control (positive) for pathogens: TS

The conventional Tryptic Soy (TS) broth (BD, 211825) without pH adjustment was chosen.

Baseline control (negative)

A diluted solution of said MRS (15% in volume), buffered or non-buffered, is chosen to ensure a survival of the lactobacilli and pathogens tested at a low level of growth or inhibition, respectively.

Medium 17 (according to the invention):

an optimized test composition according to the following Table and intended to stabilize the pH as well as allow the growth of *Lactobacillus* spp. and, at the same time, inhibition of pathogens.

| Medium 17 | Function | Substance | Origin | Concentration |
|---|---|---|---|---|
|  | preservative buffer | Ca-lactate pentahydrate | Applichem, A3670 | 20 mg/ml |
|  |  | Dibasic ammonium citrate | Sigma 09833 | 10 mg/ml |
|  | N-source (ammonium, contained in buffer) |  |  |  |
| Final pH of solution: 4.56 | Carbon source | α-Glyco-oligosaccharide | Bio-Ecolians, UCIB Solabia Group, AB020 | 20 mg/ml |
|  | Contains sulfur compounds | MRS-broth | Biolife 4017292 | 15% vol. |

Growth Conditions and Counting Procedure

All cultures were grown at 37° C. under anaerobic conditions without agitation.

A first culture was prepared from material preserved at −80° C. by streaking on agar plates. After incubation for no more than 24 hours, a single colony from the plate was used to inoculate 5 mL liquid culture and incubated for up to 18 hours and then used to inoculate 25 mL of each of the different media for the growth experiments. The starting cell density was adjusted to correspond to an optical density (600 nm) of 0.05.

All the experiments were performed in duplicate.

The growth of the cultures was monitored by measuring the optical density at 600 nm, the pH, by plating of serial dilutions on agar plates (cfu/mL) and by counting the total cell numbers using a haemato-cytometer (Neubauer improved).

Strains Tested: Vaginal *Lactobacillus* Spp. and Urogenital Pathogens

The vaginal strains tested comprise all relevant *Lactobacillus* species of the physiological vaginal microbiota, i.e. *L. gasseri*, *L. crispatus* and *L. jensenii* and in particular *L. gasseri* 120.1 CNCM I-3218, *L. gasseri* 124.3 CNCM I-3220, *L. crispatus* 119.4 CNCM I-3484 and *L. jensenii* 119.1 CNCM I-3217.

As representative pathogens in these experiments were selected:

a) Gram-negative: uropathogenic *E. coli* COOS 492, multi-resistant, human clinical isolate from University Hospital Zurich, isolated in 1976.

b) Gram-positive: multi-resistant *S. aureus*, COOS 461, MRSA, human clinical isolate, Hospital in Oxford, UK, isolated in 1960.

Uropathogenic *E. coli* is the most common strains causing cystitis. *S. aureus* is associated with vaginal infections of the type called aerobic vaginitis (AV).

Comment

As mentioned in the title of this section acidifying, preserving and nutrient factors were chosen to be used against facultative anaerobic pathogens. These can produce energy with oxygen, like aerobes, or else also anaerobically (fermenting sugars to lactic a.s.o.). *E. coli* and *S. aureus* are representatives of this class of bacteria.

Comparative Compositions

Hereafter are reported examples of compositions that, albeit having composition similar to Medium 17, do not equally well inhibit the growth of the above-mentioned pathogens.

Example 2a: Effect of a Slight Increase of pH

As a first comparative example the following Medium 11 is provided:

| Medium 11 | Substance | Origin | Concentration |
|---|---|---|---|
|  | Ca-lactate as pentahydrate | Applichem, A3670 | 20 mg/ml |
|  | Dibasic ammonium citrate | Sigma 09833 | 10 mg/ml |
|  | Tribasic ammonium citrate | Sigma | 10 mg/ml |
| Final pH of solution: 5.00 | α-Glyco-oligosaccharide | Bio-Ecolians, UCIB Solabia Group, AB020 | 20 mg/ml |
|  | MRS-broth | Biolife 4017292 | 15% vol. |

In this medium the count evolution of the pathogens mentioned above under similar experimental conditions was studied.

*E.coli* CCOS 492

|  | Medium 11 | | 100% MRS | |
|---|---|---|---|---|
| Time (h · min) | pH | Count (cfu) | pH | Count (cfu) |
| 00.00 | 5.00 | $1 * 10^5$ | 6.35 | $1 * 10^5$ |
| 06.10 | 4.98 | $8 * 10^5$ | 5.53 | $5 * 10^7$ |
| 20.20 | 4.98 | $4 * 10^5$ | 5.01 | $>1 * 10^9$ |

*S. aureus* CCOS 461

|  | Medium 11 | | 100% MRS | |
|---|---|---|---|---|
| Time (h · min) | pH | Count (cfu) | pH | Count (cfu) |
| 00.00 | 5.00 | $1 * 10^5$ | 6.35 | $1 * 10^5$ |
| 06.10 | 4.99 | $1 * 10^6$ | 5.69 | $6 * 10^7$ |
| 20.20 | 4.98 | $4 * 10^6$ | 5.05 | $>1 * 10^9$ |

Hence, an increase of the pH of 4.5 by half a unit to a final value of 5.0 is enough to allow for the growth of pathogens for more than one log, pathogens that are otherwise inhibited at, pH 4.5.

Example 2b: Effect of a Reduction of Lactate Concentration by 50%

As an embodiment, the following Medium 12 was prepared and the evolution of the count of E.coli in same medium was observed.

| Medium 12 | Substance | Origin | Concentration |
|---|---|---|---|
| | Ca-lactate as pentahydrate | Applichem, A3670 | 10 mg/ml |
| | Dibasic ammonium citrate | Sigma 09833 | 10 mg/ml |
| | Tribasic ammonium citrate | Sigma | 10 mg/ml |
| Final pH of solution: 5.18 | α-Glyco-oligosaccharide | Bio-Ecolians, UCIB Solabia Group, AB020 | 20 mg/ml |
| | MRS-broth | Biolife 4017292 | 15% vol. |

In this medium, as well as in TSA as a positive control medium, the count evolution of pathogenic E.coli COOS 492 mentioned above was studied under similar experimental conditions as in Example 2a, E.coli CCOS 492

| | Medium 12 | | TSA | |
|---|---|---|---|---|
| Time (h · min) | pH | Count (cfu) | pH | Count (cfu) |
| 00.00 | 5.18 | $1 * 10^{-5}$ | 6.7 | $1 * 10^{-5}$ |
| 06.10 | 5.21 | $4 * 10^{-6}$ | 6.1 | $5 * 10^{-7}$ |
| 20.20 | 5.23 | $8 * 10^{-6}$ | 5.5 | $>1 * 10^{-9}$ |

It appears that the reduction in lactate concentration as in Medium 12 to half the value of Medium 17 comes along with a significant reduction of the inhibitory power with respect to the latter leading to an increase of the pathogen count of almost 2 logs.

In summary, it appears that the precise concentrations of the active principles (citrate, lactate a.s.o.) as exemplified for Medium 17 are, preferable to ensure high pathogen inhibition action of the same.

Example 2: Detailed Discussion of the Results for L. Gasseri 120.1 CNCM I-3218

The in vitro model for testing the effect of the application of a pharmaceutical formulation in the vagina used in this application is that of a liquid medium containing the ingredients of the formulation at approximately the same concentration that it will have after dissolution in the vagina. The aim of the in vitro experiments to be described in the following was therefore to find a growth medium formulation that allows to install and maintain for a one-day duration a physiological pH of 4.0-4.5. Furthermore, said medium should allow the lactobacilli to rapidly establish themselves and to grow therein whereas at the same time the urogenital pathogens should be inhibited.

The cell counts of L. gasseri KS 120.1 CNCM I-3218 grown for 19.4 hours on MRS medium reached $1 \times 10^8$ du/ml, the highest value over all of the 3 media tested. As expected, a clear pH drop from 6.4 to 4.0 was observed. This control experiment indicates the good fitness of the inoculum used and that the growth curves observed in the other media are correct.

Comparing the growth obtained in Medium 17 with the MRS control, a slightly reduced growth (0.4 log units) was observed. As Medium 17 with its relatively simple composition does only contain a reduced amount of trace elements this effect was expected.

Comparing the growth in Medium 17 with that in the 15% MRS medium, a 4.9 log-level reduction in the final cell counts between these media was observed. This clearly shows that the additional nutrients and components present in Medium 17 do indeed promote the growth of the tested Lactobacillus strain.

Acidity: the pH values remain remarkably stable around 4.5 from the beginning of the experiments and up to 20 hours thereafter (varying from 4.58 to 4.41), confirming thereby the adequate strength of the buffering system.

Conclusion: the presented Medium 17 formulated according to the description of the present invention induces a significant growth of the inoculated Lactobacillus gasseri, slightly less than for pure MRS, but definitely stronger than diluted (15%) MRS. The pH of the system remains constant at the optimum targeted value of approximately 4.5.

Example 3: Detailed Discussion of the Results for S. aureus CCOS 461

The hypothesis to be tested in this case is that the chosen Medium 17 is able to inhibit the growth of the selected multi-resistant pathogen.

The cell counts of S. aureus CCOS 461 grown for 21.1 hours on TS medium reached with $2 \times 10^8$ cfu/ml the highest value over all of the 3 media tested starting with a value of $9 \times 10^{\wedge}6$ at t=0 h. Also in this case a clear pH drop from 7.0 to 4.8 was observed. This control experiment indicates a good fitness of the inoculum used and that the growth curves observed in the other media are correct.

Comparing the evolution of the cell count obtained in Medium 17 with the TS positive control, a strong inhibition of S. aureus COOS 461 of −5.2 logarithmic units was observed. With respect to diluted MRS the inhibition was also high, amounting to −4.4 logs.

Acidity: even in the presence of the live pathogen the pH values remain again remarkably stable around 4.5 from the beginning of the experiments and up to 20 hours thereafter with only a slight decrease (varying from 4.59 initially to 4.40 finally).

Conclusion: the presented Medium 17, formulated according to the description of the present invention, induces a significant decrease of the counts of the inoculated pathogen S. aureus CCOS 461: with respect to the positive control medium TS but even with respect to diluted MRS, Medium 17 shows herewith by itself an anti-microbial action against this pathogen.

Example 4: Summary of the Experimental Series

The results of the remaining strains mentioned above in Example 2 shall be presented in tabular form together with the two last examples and commented upon.

Preliminary remarks: All 4 lactobacilli tested showed the same trend: good growth on Medium 17, reduced growth on 15% MRS broth and excellent growth in the control medium of MRS broth. A drop in pH in the non-buffered media (15% MRS and pure MRS) was also observed.

For all 4 Lactobacillus strains and the 2 pathogens the pH-values, designed to be buffered at a value of 4.5, the measurements confirm the excellent stability of the acidity of the medium for up to 20 hours or more of reaction time.

The pathogens S. aureus and E. coli as well were clearly not able to grow in Medium 17. The corresponding cell concentrations in this medium decreased dramatically in time.

TABLE Ex. 4 pH values in Medium 17 and log (reduction or increase) of cell numbers of the tested organisms grown on Medium 17 (according to the invention) against the reference media

| Strain | Time | Log change of cfu/mL on Medium 17 versus | | | pH-value Medium 17 | |
|---|---|---|---|---|---|---|
| | | 15% MRS | MRS | TSB | initial | final |
| KS 119.4 CNCM I-3484 | 28.6 h | 0.57 | −0.49 | | 4.57 | 4.33 |
| KS 119.1 CNCM I-3217 | 18.6 h | 1.12 | −2.15 | | 4.59 | 4.37 |
| KS 120.1 CNCM I-3218 | 19.4 h | 4.94 | −0.40 | | 4.58 | 4.44 |
| KS 124.3 CNCM I-3220 | 28.6 h | 0.44 | −0.90 | | 4.57 | 4.33 |
| CCOS 461 | 21.1 h | −4.44 | | −5.19 | 4.59 | 4.40 |
| CCOS 492 | 22.1 h | −5.70 | | −8.13 | 4.49 | 4.42 |

In Table Ex. 4, the differences in log numbers at the end of the respective growth experiments are summarized. The strongest growth promoting effect was observed in *Lactobacillus gasseri* KS 120.1 CNCM I-3218 with almost 5 log-levels increase compared to 15% MRS, whereas the weakest effect was found in *Lactobacillus gasseri* KS 124.3 CNCM I-3220, with a log-level increase of only 0.44. Overall conclusion: During the fermentation process Medium 17 did stabilize the pH at a value between 4.5 and 4.3 for all strains tested. As to the *Lactobacillus* strains: they grew better on Medium 17 than on 15% MRS medium. In this particular medium the addition of ammonium citrate as an additional nitrogen source and of calcium-lactate as buffer substance, as well as the use of a selective carbon source (in this particular case glyco-oligosaccharide) for the probiotics proved to be sufficient to stimulate differentially the growth of the tested lactobacilli. On the other hand the 2 tested pathogens (*E.coli* and *S. aureus*) did not grow on "Medium 17" but were inhibited by the same Example 5

Out of the systematic experiments leading to the proper media such as Medium 17 described above, the quantitative composition of a pharmaceutical dosage unit (capsule, tablet . . . ) to be applied intra-vaginally can be calculated. As mentioned above this requires to quantitatively take into account the volume of the vaginal fluid, a quantity that obviously varies according to the age and health conditions of the woman. Research has found that the volume of such fluid is around 3 ml on average (Ref. 16).

TABLE Ex. 5.1 quantitative composition of a prebiotic vaginal capsule according to the invention

| Capsule #6 | Substance | Amount |
|---|---|---|
| | Ca-lactate pentahydrate | 60 mg |
| | Dibasic ammonium citrate | 30 mg |
| | α-Glyco-oligosaccharide | 100 mg |
| Target pH in vagina: 4.5 | Glutamic acid | 40 mg |
| | Cystein or Cystin | 20 mg |
| | Excipients as required | 200 mg |
| | Total weight | 450 mg |

TABLE Ex. 5.2 quantitative composition of vaginal capsule according to the invention

| Tablet #8 | Substance | Amount |
|---|---|---|
| | Lyophilisates of vaginal strains *L. gasseri* 120.1 and 124.3 at concentrations of $10^{11}$ cfu/g | 100 mg |
| | Ca-lactate pentahydrate | 60 mg |
| | Dibasic ammonium citrate | 30 mg |
| | Arabinogalactan | 100 mg |
| Target pH in vagina: approx. 4.5 | Thiosulfate | 30 mg |
| | Excipients as required | 270 mg |
| | Total weight | 600 mg |

TABLE EX 5.3 quantitative composition of vaginal capsule according to the invention

| Tablet #9 | Substance | Amount |
|---|---|---|
| | Ca-lactate pentahydrate | 60 mg |
| | Dibasic magnesium citrate | 30 mg |
| | Arabinogalactan | 100 mg |
| Target pH in the vaginal preparation: approx. 4.5 | Thiosulfate | 30 mg |
| | Aspartic acid | 60 mg |
| | Excipients as required | 270 mg |
| | Total weight excipients/additives | 550 mg |
| | Lyophilisate of *L. gasseri* KS 120.1 CNCM I-3218 | 50 mg |
| | Lyophilisate of *L. jensenii* 119.1 CNCM I-3484 | 50 mg |
| | Lyophilisate of *L. crispatus* KS 119.4 CNCM I-3217 | 50 mg |
| | Total weight including lyophilisates | 700 mg |

TABLE Ex. 5.4 quantitative composition of an oral symbiotic preparation (sachets) according to the invention

| Sachets #9 | Substance | Amount |
|---|---|---|
| | Ca-lactate pentahydrate | 100 mg |
| | Dibasic magnesium citrate | 50 mg |
| | Alpha-glyco-oligosaccharide | 1,000 mg |
| Target pH in the oral preparation when dissolved in 150 ml water: 4.5 | Arabinogalactan | 1,000 mg |
| | Thiosulfate | 30 mg |
| | Aspartic acid | 60 mg |
| | Alanine | 60 mg |
| | Excipients as required | 350 mg |
| | Total weight excipients/additives | 2,650 mg |
| | Lyophilisate of *L. gasseri* KS 120.1 CNCM I-3218 | 50 mg |
| | Lyophilisate of *L. jensenii* 119.1 CNCM I-3217 | 50 mg |
| | Lyophilisate of *L. crispatus* KS 119.4 CNCM I-3484 | 50 mg |
| | Total weight including lyophilisates | 2,850 mg |

TABLE Ex. 5.5 quantitative composition of a prebiotic vaginal lubricant according to the invention

| Lubricant gel # 3 | Substance | Amount |
|---|---|---|
| | Lactic acid | 50 mg |
| Target pH of the finished gel = 4.5 | Citric acid | 30 mg |
| | Glycerol | 80 mg |
| | Carbomer | 5 mg |
| | Short-chain fructo-oligo-saccharides | 50 mg |
| | Thiosulphate | 10 mg |
| | Glutamic acid | 10 mg |
| | NaOH 0.1 mol or HCl 0.1 mol for pH = 4.5 | q.s. |
| | De-ionized water | ad 1,000 mg |

Optimizing the Redox Potential of the Vaginal Fluid

In the Example 5.1 above, the sulfur source added to M17 is cysteine or cystin, in Example 5.2 it is sodium thiosulfate. All the above-identified 3 formulations lead e.g. to a pH value of the corresponding solution in 2-5 ml of about 4.5. From the point of view of acidity, nutrients, preservative they look very similar.

The question we raise now is whether they are equivalent with respect to the task assigned to them, that is to foster the growth of lactobacilli in the vagina and inhibit that of pathogens. To specify this question, we have to focus on specific pathogens; we shall choose the most frequent vaginal infection as mentioned above, the so called bacterial vaginosis or BV associated with pathogens like *Gardnerella vaginalis* or *Prevotella bivia*. In 1985 David Eschenbach and coworkers published a research paper (Ref. 22) in which they investigated the correlation between bacterial vaginosis and the vaginal redox potential respectively the pH.

On one hand they confirmed, as expected, that in the 15 patients a pH in the range 4.0 to 4.5 is mostly associated with a healthy vaginal microbiota, whereas in the range 4.5 to 5.5 the patients exhibit a strong presence of anaerobes with few lactobacilli and the symptoms of BV. The novelty was that they can also show that also the redox potential Eh in the vagina is in vivo strongly dependent on the status of the microbiota: Whereas the Eh values in the BV patients range between +50 and −250 mV, the Eh values of the healthy vaginas range higher between 100 and 300 mV. They also found that this is not a characteristic of the individual women, but was only dependent on the status of the microbiota. After a successful cure with metronidazole all women with a negative redox potential returned to a positive one (and also the pH returned to be more acidic).

Interestingly there have been no attempts to therapeutically use this fact to produce vaginal pharmaceutical products for treating BV, which warrant a higher redox potential.

We investigated this opportunity by the following experimental procedure:

Summary of the Test Procedure

A media formulation consisting of 20 mg/mL Ca-Lactate, 10 mg/mL dibasic ammonium citrate, 20 mg/mL Ecolians and 15% MRS broth was prepared (corresponding to M17 described above). After measurement of redox potential and pH several compounds (nitrogen and sulphur sources) were added to this medium and their effect on pH and redox potential was determined.

Brief Description of the Experiments

A redox electrode (Mettler Toledo LE 501 ORP, connected to a pH-Meter MP230, Mettler Toledo) was used to measure the redox potential of the media formulation before and after addition of the test compounds. Redox values were read after the signal was stable for at least 30 seconds. In addition the pH was measured using a standard pH Electrode connected to a MP225 pH Meter (Mettler Toledo).

Prior to each measurement series, the redox electrode was calibrated using a reference solution (Mettler Toledo, no 51350060, 220 mV, pH 7 (UH=427 mV)).

Analysis Results

| Setup | Konz. | Substanz | pH | Redox | Referenz |
|---|---|---|---|---|---|
| 1 | 20 mg/mL | Ca-Lactate | 4.67 | 235.0 mV | 236.2 mV |
| | 10 mg/mL | Ammoniumcitrate, dibasic | | | |
| | 15% | MRS-Broth | | | |
| | 20 mg/mL | Ecolians | | | |
| | 10 mg/mL | L-Glutamic acid | 4.48 | 310.8 mV | |
| 2 | 20 mg/mL | Ca-Lactate | 4.67 | 235.0 mV | 236.2 mV |
| | 10 mg/mL | Ammoniumcitrate, dibasic | | | |
| | 15% | MRS-Broth | | | |
| | 20 mg/mL | Ecolians | | | |
| | 10 mg/mL | L-Glutamic acid | 4.41 | 265.2 mV | |
| | 10 mg/mL | Cystin | | | |
| 3 | 20 mg/mL | Ca-Lactate | 4.67 | 235.0 mV | 236.2 mV |
| | 10 mg/mL | Ammoniumcitrate, dibasic | | | |
| | 15% | MRS-Broth | | | |
| | 20 mg/mL | Ecolians | | | |
| | 10 mg/mL | L-Glutamic acid | 4.30 | −103.0 mV | |
| | 10 mg/mL | Cysteine | | | |
| 4 | 20 mg/mL | Ca-Lactate | 4.67 | 235.0 mV | 233.0 mV |
| | 10 mg/mL | Ammoniumcitrate, dibasic | | | |
| | 0% | MRS-Broth | | | |
| | 20 mg/mL | Ecolians | | | |
| | 10 mg/mL | L-Glutamic acid | 4.26 | 284.2 mV | |
| | 20 mg/mL | Na-Thiosulfate | 4.21 | −36.5 mV | |
| 5 | 20 mg/mL | Ca-Lactate | 4.48 | 237.8 mV | 234.9 mV |
| | 15 mg/mL | Ammoniumcitrate, dibasic | | | |
| | 0% | MRS-Broth | | | |
| | 20 mg/mL | Ecolians | | | |
| | 10 mg/mL | L-Glutamic acid | 4.27 | 301.3 mV | |
| | 20 mg/mL | Dimethylsulfone | 4.26 | 273.3 mV | |

Comments
- Addition or not of 15% MRS to the solution has practically no effect on pH or Eh
- Addition of the nitrogen source glutamic acid renders the medium slightly more acidic and more electropositive/oxydative reaching 300 mV
- The sulfur compounds have. In this particular experimental series the most marked effect of the redox potential and a minor effect on the acidity: compare e.g. setup 2 and setup 3, where cysteine and cystin are interchanged. With cysteine the Eh decreases to −103.0 mV, whereas with the same amount cysteine it increases to 265.2 mV. The pH on its side varies only minimally, from 4.30 to 4.41. Cystine (the oxidized dimeric form of cysteine) and MSM (dimethylsulfone) both maintain a high positive redox potential, whereas Cysteine and thiosulfate cause the solution to become reducing instead of oxidizing, reaching negative values of −103 and −36 mV The conclusion is that adding e.g. cysteine or thiosulfate an environment favorable to the proliferation of anaerobes is obtained, whereas adding cystin or dimethylsulfone helps creating an environment favorable to the development of lactobacilli. This is of therapeutic interest as we can by such means choose not only which pH, but also which redox potential is best suited to fight locally a defined pathogen. By using a proper "redox modulator" the efficacy of the anti-BV formulation according to the invention can thus be increased.

The above considerations apply against the pathogens of BV (*Gardnerella, Prevotella, Atopobium*, which are by nature "obligate anaerobes", i.e microbes who cannot defend themselves against oxydants as, e.g. hydrogen peroxide or other oxidative agents. Against these pathogens increasing the redox potential is an additional therapeutic weapon. This works without damaging or inhibiting the vaginal lactobacilli: the reason being that the lactobacilli, although being themselves anaerobs, are so-called "aero tolerants". That is, oxygen and more generally an environment with high redox potential ($E_h$) does not prevent them from growing.

Choosing a Redox Modulator

Preferably, in the context of the present invention the term "redox modulator" indicates a substance, or at least a pair of substances, capable of reducing or enhancing the redox potential of a certain biological medium. Preferably, the redox modulator e) is chosen among sulphur-containing compounds the pair cysteine/cystin, like N-acetyl cysteine, cysteine, methionine, quinone/hydroquinone, selenium-based redox systems (selenite/selenate, e.g. in the sodium salt form), sodium thiosulphate/bisulphite, glutathione in the reduced state (GSH) and in the oxidized state (GSSG). For example, if the redox potential needs to be enhanced so as to become definitely positive (>150 mV) and to inhibit anaerobs like *Gardnerella*, cystin (the oxidized form) will be chosen for this purpose rather than cysteine.

Concrete examples of anti-BV formulations with enhanced oydation potential

Example 6.1: Prebiotic Formulation

TABLE Ex. 6.1 quantitative composition of a prebiotic vaginal capsule against BV according to the invention

| Capsule #10 | Substance | Amount |
|---|---|---|
| Target Eh in vaginal fluid: >200 mV | Ca-lactate pentahydrate | 60 mg |
| | Dibasic magnesium citrate | 30 mg |
| | α-Glyco-oligosaccharide | 100 mg |
| Target pH in vagina: 4.5 | Glutamic acid | 40 mg |
| Redox modulator and S-source | Cystin | 20 mg |
| | Excipients as required | 200 mg |
| | Total weight | 450 mg |

Example 6.2: Symbiotic Formulation Against Anaerobic Vaginal Infection According to the Invention TABLE Ex. 6.2 quantitative composition of a symbiotic vaginal capsule against BV

| Tablet #11 | Substance | Amount |
|---|---|---|
| Strains with proven, pronounced activity against Gardnerella | Lyophilisates of vaginal strains *L. gasseri* 120.1 and 124.3 at concentrations of $10^{11}$ cfu/g | Each 100 mg |
| Target oxidation potential in vagina:: >200 mV | Ca-lactate pentahydrate | 60 mg |
| | Dibasic magnesium citrate | 30 mg |
| | Alanin | 40 mg |
| | Arabinogalactan | 100 mg |
| Target pH in vagina: approx.. 4.5 | Dimethylsulfone (MSM) | 30 mg |
| | Excipients as required | 140 mg |
| | Total weight | 600 mg |

Eradicating *Candida Albicans*

As mentioned above *Candida* is a frequently observed microbe in the vagina, either as an opportunistic agent or as pathogen, e.g. appearing after an anti-infective treatment of vaginal infections such as bacterial vaginosis. The peculiarity of *Candida* is that, unlike the anaerobic pathogens involved in BV, they can co-exist with Lactobacilli, thereby exerting only an effect on the composition of the vaginal microbiota. The composition of the Döderlein flora under these 3 different states (no infection, BV or Candidiasis has been investigated recently in detail and published by G. Donders and co-workers (Ref. 23).

For the above-mentioned reasons the authors thought that it would be useful, if feasible, to shape the composition intended to foster lactobacilli but at the same time to inhibit pathogens, such as to have an inhibitory effect also on yeasts in general and *Candida albicans* in particular.

It would be tempting to use to this purpose a classical and safe antifungal drug like Clotrimazole, this molecule has however also a bactericidal activity against Gram-positive bacteria such as Lactobacilli are (Ref. 24"). In searching for a suitable molecule for our intended purpose we found a naturally occurring organic acid (sorbic acid) that is widely used as safe preservative agent against yeast and mould degradation in the food and pharmaceutical industry. The issue was therefore to test whether sorbic acid (usually available as sodium or potassium sorbate) was able to inhibit *Candida* at concentrations that were non inhibiting for the vaginal lactobacilli. The reported optimum for the activity of sorbate is around pH 4.5, which fits perfectly in our chosen range. The concentration practically used for preservation against yeasts and molds is of 0.1% (Ref. 25).

To this end the following experiments were performed.

Summary of the Test Procedure

A fresh overnight culture of the test strains was used to inoculate the test medium supplemented with different concentrations of potassium sorbate. Growth was determined by measurement of optical density and pH at start, after 6 hours and after 24 hours.

Growth Conditions:

Medium for overnight culture: MRS broth with Tween
Test medium: MRS broth with Tween, diluted to 30%, pH adjusted to 4.5 with lactic acid -continued

| | |
|---|---|
| Testvolume: | 5 ml |
| Incubation: | 37° C., anaerob, with shaking (120 rpm) |
| Cell density for inoculation: | approx. $10^7$ cfu/ml |
| Potassium sorbate concentrations: | 0.00%, 0.01%, 0.05%, 0.1%, 0.5%, 1.0%, 1.5% (weight/volume) |
| Measurement parameters: | pH, 0 D at 590 nm |
| Measurements at: | t = 0 h, 6 h and 24 h |

Tested Bacterial Cultures

Lactobacillus gasseri CCOS 960, Lactobacillus gasseri KS 121.1, Lactobacillus crispatus KS 116.1

Preparation of Cultures

All cultures were re-activated from cryopreserved (−80° C.) working stocks by cultivation on MRS agar for 1 to 3 days. A single colony from these plates was used to inoculate 5 ml of MRS broth. After incubation overnight, $10^7$ cfu/ml were used to carry out the experiments.

Analysis Results

| Strain | Potassium Sorbate Concentration | OD 0 h | OD 6 h | OD 24 h | pH 0 h | pH 6 h | pH 24 h | Interpretation |
|---|---|---|---|---|---|---|---|---|
| Lactobacillus | 0.00% | 0.51 | 0.84 | 1.26 | 4.71 | 4.57 | 4.27 | 0 |
| gasseri | 1.00% | 0.54 | 0.78 | 0.97 | 5.16 | 5 | 5.07 | 1 |
| KS 120.1 | 1.50% | 0.53 | 0.73 | 0.72 | 5.31 | 5.26 | 5.26 | 1 |
| Lactobacillus | 0.00% | 0.12 | 0.54 | 0.68 | 4.51 | 4.49 | 4.41 | 0 |
| jensenii | 0.10% | 0.08 | 0.23 | 0.44 | 4.5 | 4.5 | 4.5 | 0 |
| KS 119.1 | 0.50% | 0.07 | 0.11 | 0.124 | 4.5 | 4.5 | 4.85 | 1 |
| | 1.00% | 0.18 | 0.26 | 0.16 | 5.03 | 5.01 | 5.09 | 2 |
| | 1.50% | 0.17 | 0.24 | 0.13 | 5.32 | 5.18 | 5.25 | 2 |
| Lactobacillus | 0.00% | 0.72 | 1.36 | 1.36 | 4.73 | 4.5 | 4.37 | 0 |
| crispatus | 0.01% | 0.7 | 1.36 | 1.47 | 4.71 | 4.42 | 4.35 | 0 |
| KS 119.4 | 0.05% | 0.6 | 1.16 | 1.24 | 4.69 | 4.43 | 4.32 | 0 |
| | 0.10% | 0.68 | 1.34 | 1.24 | 4.7 | 4.48 | 4.44 | 0 |
| | 0.50% | 0.67 | 1.24 | 1.15 | 4.97 | 4.73 | 4.77 | 0 |
| | 1.00% | 0.65 | 1.13 | 0.96 | 5.8 | 5.01 | 5.08 | 1 |
| | 1.50% | 0.64 | 0.99 | 0.76 | 5.32 | 5.2 | 5.26 | 1 |

Interpretation:
0: no inhibition,
1: slight inhibition,
2: strong inhibition

Conclusions

For a strong inhibitory effect on the growth of the tested lactobacilli a minimum concentration of potassium sorbate of 1% (or 10 mg/ml), for a slight inhibition 0.5% or higher was required.

According to Kramer and Assadian (Ref 25) the microbiostatic concentration for the inhibition of growth of pathogenic bacteria and fungi is much lower (S. aureus, E. coli, K. pneumoniae: 50-100 µg/ml, Penicillium notatum, Aspergillus niger: 200-500 µg/ml, Saccharomyces cerevisiae: 50-100 µg/ml).

The tested lactobacilli (gasseri, crispatus and jensenii) which represent the standard Döderlein flora should therefore be able to sustain their growth in the presence of concentrations of up to 0.1-0.2% (1.5 to 3 mg/ml) of potassium sorbate.

Transformed into a formula of a capsule that will be dissolved in approximately 3 ml of vaginal fluid this corresponds to the addition of 3 to 6 mg potassium sorbate to the composition (see below).

Example 7.1: Formulation Against Obligate Anaerobic Pathogens with Anti-*Candida* Activity as Well TABLE Ex. 7.1 quantitative composition of prebiotic vaginal capsule according to the invention without lyophilisates and containing also sorbate as antifungal ingredient

| Capsule #12 | | Substance | Amount |
|---|---|---|---|
| | | Ca-lactate pentahydrate | 60 mg |
| | | Dibasic magnesium citrate | 30 mg |
| | | a-Glyco-oligosaccharide | 100 mg |
| Target pH in vagina: | | Glutamic acid | 40 mg |
| 4.5 | | Cystin | 30 mg |
| | | K-sorbate | 5 mg |
| | | Excipients as required | 185 mg |
| | | Total weight | 450 mg |

TABLE Ex. 7.2 quantitative composition of vaginal capsule according to the invention containing lyophilisates and also potassium sorbate as antifungal agent

| Tablet #11 | Substance | Amount |
|---|---|---|
| | Lyophilisates of vaginal strains L. gasseri 120.1 and 124.3 at concentrations of $10^{11}$ cfu/g | 100 mg each |
| | Ca-lactate pentahydrate | 60 mg |
| | Dibasic ammonium citrate | 30 mg |
| | K-Sorbate | 5 mg |
| | Arginin | 20 mg |
| | Arabinogalactan | 100 mg |
| Target pH in vagina: | Cystin | 30 mg |
| 4.5 | Excipients as required | 155 mg |
| | Total weight | 600 mg |

Example 7.3: Lubricant Prebiotic Formulation with Activity Against BV and Candida TABLE Ex. 7.3 quantitative composition of a prebiotic vaginal lubricant according to the invention

| Lubricant gel # 3 | Substance | Amount |
|---|---|---|
|  | Lactic acid (D- or racemic) | 50 mg |
| Target pH of the | Citric acid | 30 mg |
| finished gel = 4.5 | Glycerol | 80 mg |
|  | Carbomer | 5 mg |
|  | Short-chain fructo-oligo-saccharides | 50 mg |
|  | MSM | 20 mg |
| Target oxidation | Glutamic acid | 20 mg |
| potential: | NaOH 0.1 mol or HCl 0.1 mol | q.s. |
| >150 mV | for pH = 4.5 |  |
|  | De-ionized water | ad 1,000 mg |

REFERENCES CITED

1. Krauss-Silva L., Almada-Horta A., Alves M. B., Camacho K. G., Moreira M. E. L., Braga A. 2014. Basic vaginal pH, bacterial vaginosis and aerobic vaginitis: prevalence in early pregnancy and risk of spontaneous preterm delivery, a prospective study in a low socioeconomic and multi-ethnic South American population. BMC Pregnancy and Childbirth 14:107.
2. Donders G. G., Vereecken A., Bosmans E., Dekeersmaecker A., Salembier G., Spitz B. 2002. Definition of a type of abnormal vaginal microbiota that is distinct from bacterial vaginosis: aerobic vaginitis. BJOG. 109(1):34-43.
3. www.patient.co.uk/doctor/bacterial-vaginosis-pro (21.05.2015). Up to 70% of patients have a relapse within three months of successful treatment.
4. Döderlein A. 1892. Das Scheidensekret and seine Bedeutung für das Puerperalfieber. Zbl. Bakteriol. 11: 699.
5. Spurbeck R. R., Arvidson C. G. 2011. Lactobacilli at the front line of defense against vaginally acquired infections. Future Microbiology 6(5): 567-582.
6. Atassi F., Brassart D., Grob P., Graf F., Servin A. L. 2006. Lactobacillus strains isolated from the vaginal microbiota of healthy women inhibit Prevotella bivia and Gardnerella vaginalis in coculture and cell culture. FEMS Immunol Med Microbio 48 (3) 424-432.
7. Atassi F., Brassart D., Grob P., Graf F., Servin A. L. 2006. Vaginal Lactobacillus isolates inhibit uropathogenic Escherichia coli. FEMS Microbiol Lett 257 (1): 132-135.
8. EP 1 812 023 B1, F. Graf June 2004, EP 2 561 880 B1, F. Graf June 2004.
9. Reid et al, U.S. Pat. No. 5,645,830, July 1997.
10. De Man J. C., Rogosa M., Sharpe M. E. 1960. A medium for the cultivation of lactobacilli. Journal of Applied Bacteriology 23(1): 130-135.
11. Chrisope G et al, Gynelogix Inc WO 9846261 www.disknet.com/indiana_biolab/b028.htm_(21.05.2015).
12. www.cdc.gov/std/treatment/2010/vaginal-discharge.htm.
13. ELLEN A B, Darviczky K et al, 2010, WO2010023222.
14. Procter&Gamble Co, Carella A M et al, 1997 WO9729763.
15. Laxmi N. P., Mutamed M. A., Nagendra P. S 2011, Effect of carbon and nitrogen sources on growth of Bifidobacterium animalis BB12 and Lactobacillus delbrueckii ssp. bulgaricus ATCC 11842 and production of β-galactosidase under different culture condition. International Food Research Journal 18: 373-380.
16. Eschenbach D. A., Thwin S. S., Patton D. L., Hooton T. M., Stapleton A. E., Agnew K., Winter C., Amalia Meier A., Walter E. Stamm W. E. 2000, Influence of the Normal Menstrual Cycle on Vaginal Tissue, Discharge, and Micromicrobiota. Clinical Infectious Diseases 30(6): 901-907.
17. Gut. 1988 Aug.; 29(8):1035-41. Measurement of gastrointestinal pH profiles in normal ambulant human subjects. Evans D F, Pye G, Bramley R, Clark A G, Dyson T J, Hardcastle J D.
18. Gut Microbes Volume 7, Issue 3, 2016 Special Issue: Gut Microbiota Metabolites in Health and Disease, Douglas J. Morrison & Tom Preston, pages 189-200.
18a. Maria Elli et al, EP1038951 A1, Société Des Produits Nestlé S. A.
19. de.wikipedia.org/wiki/Joghurt.
20. The Journal of Infectious Diseases, Volume 180, Issue 6, pp. 1950-1956. May A. D, Antonio[1], Stephen E. Hawes[3] and Sharon L. Hillier[1].
21. Use and procurement of additional lubricants with male and female condoms: WHO/UNFPA/FHI360—Advisory Note, apps.who.int/iris/bitstream/10665/76580/1/WHO_RHR_12.33_eng.pdf, WHO 2012.
22. The Journal of Infectious Diseases VOL. 152, No. 2, 1985, K. H. Holmes, K. C. S. Chen, C. M. Lipinsky and D. A. Eschenbach.
23. B. Vitali et al., Environ. Microbiol. September 2007, Vol. 73 No. 18, 5731-5741.
24. P. R. Sawyer et al., Drugs 1975, Vol. 9, Issue 6, pp. 424-447, "Clotrimazole: A Review of its Antifungal Activity and Therapeutic Efficacy.
25. Kramer A., Assadian O. (Eds.) 2008. Wallhäußers Praxis der Sterilisation, Antiseptik and Konservierung. Georg Thieme Verlag. Stuttgart.

The invention claimed is:
1. A method for treating or preventing urogenital infections caused by pathogenic microorganisms in a female subject, comprising the following steps:
 (a) providing a composition having a pH from 4.3 to 4.6 comprising the following ingredients per single dosage:
  i) calcium-lactate pentahydrate: 30-90 mg,
  ii) dibasic magnesium citrate: 15-45 mg,
  iii) prebiotic fiber: 15-150 mg,
  iv) glutamic acid: 20-60 mg,
  v) cystine or thiosulfate: 10-50 mg, and
  vi) excipients to 400-1100 mg; and
 (b) administering the composition intravaginally to the subject in need of treatment.
2. The method according to claim 1, wherein the composition comprises:
  i) calcium-lactate pentahydrate: 60 mg;
  ii) dibasic magnesium citrate: 30 mg;
  iii) prebiotic fiber: 100 mg;
  iv) glutamic acid: 40 mg;
  v) cystine or thiosulfate: 30 mg; and
  vi) excipients to 400-1100 mg.
3. A formulation suitable for oral administration having a pH ranging from 4.3 to 4.6 comprising an effective amount of a composition comprising Ca-lactate pentahydrate, dibasic magnesium citrate, prebiotic fiber, glutamic acid, cysteine or thiosulfate, and an excipient, wherein the amount of the composition is effective for treating or preventing urogenital infections caused by pathogenic microorganisms in a female subject.

4. The formulation of claim 3, wherein the composition comprises the following ingredients per single dosage:
   i) calcium-lactate pentahydrate: 30-90 mg;
   ii) dibasic magnesium citrate: 15-45 mg;
   iii) prebiotic fiber: 15-150 mg;
   iv) glutamic acid: 20-60 mg;
   v) cystine or thiosulfate: 10-50 mg; and
   vi) excipients to 400-1100 mg.

5. The formulation of claim 4 wherein the formulation comprises:
   i) calcium-lactate pentahydrate: 60 mg;
   ii) dibasic magnesium citrate: 30 mg;
   iii) prebiotic fiber: 100 mg;
   iv) glutamic acid: 40 mg;
   v) cystine or thiosulfate: 30 mg; and
   vi) excipients to 400-1100 mg.

6. The method according to claim 1, wherein the composition is a lubricant gel, a capsule, a tablet, a suppository, a cream, or a gel.

7. The formulation according to claim 3, wherein the formulation is in the form of a freeze-dried preparation, cream, paste, gel liquid, suppository, capsule, or tablet/stylus configured for intestinal, urethral or vaginal application.

8. The method according to claim 1, wherein the composition further comprises one or more lactobacilli strains selected from the group consisting of *L. gasseri, L. jensenii, L. crispatus, L. acidophilus, L. helveticus, L. plantarum, L. fermentum, L. lactis, L. johnsonii* and *L. acidophilus* KS 400.

9. The formulation according to claim 3, wherein the formulation further comprises at least one lactobacilli strain selected from the group consisting of *L. gasseri, L. jensenii, L. crispatus, L. acidophilus, L. helveticus, L. plantarum, L. fermentum* and *L. johnsonii*.

10. The method according to claim 8, wherein said *Lactobacillus* strain is selected from the group consisting of *L. jensenii* KS 109, *L. gasseri* KS 114.1 deposited by Medinova AG at Collection Nationale de Cultures de Microorganismes on Jul. 22, 2005 with accession number CNCM I-3482, *L. crispatus* 116.1 deposited by Medinova AG at Collection Nationale de Cultures de Microorganismes (CNCM) on Jul. 22, 2005 with accession number CNCM I-3483, *L. jensenii* KS 119.1 deposited by Medinova AG at Collection Nationale de Cultures de Microorganismes (CNCM) on Jun. 4, 2004 with accession number CNCM I-3217, *L. crispatus* 119.4 deposited by Medinova AG at Collection Nationale de Cultures de Microorganismes (CNCM) on Jul. 22, 2005 with accession number CNCM I-3484, *L. gasseri* 120.1 deposited by Medinova AG at Collection Nationale de Cultures de Microorganismes (CNCM) on Jun. 4, 2004 with accession number CNCM I-3218, *L. jensenii* KS 121.1 deposited by Medinova AG at Collection Nationale de Cultures de Microorganismes (CNCM) on Jun. 4, 2004 with accession number CNCM I-3219, *L. jensenii* KS 122.1, *L. gasseri* 123.1 deposited by Medinova AG at Collection Nationale de Cultures de Microorganismes (CNCM) on Jul. 22, 2005 with accession number CNCM I-3485, *L. gasseri* 124.3 deposited by Medinova AG at Collection Nationale de Cultures de Microorganismes (CNCM) on Jun. 4, 2004 with accession number CNCM I-3220, *L. gasseri* 126.2, *L. crispatus* 127.1 deposited by Medinova AG at Collection Nationale de Cultures de Microorganismes (CNCM) on Jul. 22, 2005 with accession number CNCM I-3486, *L. jensenii* KS 130.1, *L. helveticus* KS 300 deposited by Medinova AG at Collection Nationale de Cultures de Microorganismes (CNCM) on Feb. 10, 2005 with accession number CNCM I-3360 and *L. acidophilus* KS 400.

11. The formulation according to claim 9, wherein said *Lactobacillus* strain is selected from the group consisting of *L. jensenii* KS 109, *L. gasseri* KS 114.1 deposited by Medinova AG at Collection Nationale de Cultures de Microorganismes on Jul. 22, 2005 with accession number CNCM I-3482, *L. crispatus* 116.1 deposited by Medinova AG at Collection Nationale de Cultures de Microorganismes (CNCM) on Jul. 22, 2005 with accession number CNCM I-3483, *L. jensenii* KS 119.1 deposited by Medinova AG at Collection Nationale de Cultures de Microorganismes (CNCM) on Jun. 4, 2004 with accession number CNCM I-3217, *L. crispatus* 119.4 deposited by Medinova AG at Collection Nationale de Cultures de Microorganismes (CNCM) on Jul. 22, 2005 with accession number CNCM I-3484, *L. gasseri* 120.1 deposited by Medinova AG at Collection Nationale de Cultures de Microorganismes (CNCM) on Jun. 4, 2004 with accession number CNCM I-3218, *L. jensenii* KS 121.1 deposited by Medinova AG at Collection Nationale de Cultures de Microorganismes (CNCM) on Jun. 4, 2004 with accession number CNCM I-3219, *L. jensenii* KS 122.1, *L. gasseri* 123.1 deposited by Medinova AG at Collection Nationale de Cultures de Microorganismes (CNCM) on Jul. 22, 2005 with accession number CNCM I-3485, *L. gasseri* 124.3 deposited by Medinova AG at Collection Nationale de Cultures de Microorganismes (CNCM) on Jun. 4, 2004 with accession number CNCM I-3220, *L. gasseri* 126.2, *L. crispatus* 127.1 deposited by Medinova AG at Collection Nationale de Cultures de Microorganismes (CNCM) on Jul. 22, 2005 with accession number CNCM I-3486, *L. jensenii* KS 130.1, *L. helveticus* KS 300 deposited by Medinova AG at Collection Nationale de Cultures de Microorganismes (CNCM) on Feb. 10, 2005 with accession number CNCM I-3360 and *L. acidophilus* KS 400.

12. The method according to claim 1, wherein the composition comprises a *Lactobacillus* strain selected from the group consisting of *L. jensenii* KS 119.1 deposited by Medinova AG at Collection Nationale de Cultures de Microorganismes (CNCM) on Jun. 4, 2004 with accession number CNCM I-3217, *L. crispatus* 119.4 deposited by Medinova AG at Collection Nationale de Cultures de Microorganismes (CNCM) on Jul. 22, 2005 with accession number CNCM I-3484, *L. gasseri* 120.1 deposited by Medinova AG at Collection Nationale de Cultures de Microorganismes (CNCM) on Jun. 4, 2004 with accession number CNCM I-3218 and *L. gasseri* 124.3 deposited by Medinova AG at Collection Nationale de Cultures de Microorganismes (CNCM) on Jun. 4, 2004 with accession number CNCM I-3220.

13. The formulation according to claim 3, wherein the composition comprises a *Lactobacillus* strain selected from the group consisting of *L. jensenii* KS 119.1 deposited by Medinova AG at Collection Nationale de Cultures de Microorganismes (CNCM) on Jun. 4, 2004 with accession number CNCM I-3217, *L. crispatus* 119.4 deposited by Medinova AG at Collection Nationale de Cultures de Microorganismes (CNCM) on Jul. 22, 2005 with accession number CNCM I-3484, *L. gasseri* 120.1 deposited by Medinova AG at Collection Nationale de Cultures de Microorganismes (CNCM) on Jun. 4, 2004 with accession number CNCM I-3218 and *L. gasseri* 124.3 deposited by Medinova AG at Collection Nationale de Cultures de Microorganismes (CNCM) on Jun. 4, 2004 with accession number CNCM I-3220 and *L. acidophilus* KS 400.

14. The method according to claim 1, wherein the composition further comprises an effective amount of an anti-infective agent capable of inhibiting or eradicating urogenital pathogens selected from parasites, protozoa, bacteria, viruses, fungi or combination thereof.

15. The method according to claim 1, wherein the composition further comprises an effective amount of an antifungal agent capable to inhibiting or eradicating fungi in the urogenital area.

16. The method according to claim 15, wherein the antifungal agent is sorbic acid or salts thereof.

17. The method according to claim 1, wherein the prebiotic fiber is a non-digestible carbohydrate selected from fructo-oligosaccharides, galacto-oligosaccharides, glycol-oligosaccharides, and mixtures thereof.

18. The formulation according to claim 3, wherein the prebiotic fiber is a non-digestible carbohydrate such as: fructo-oligosaccharides, galacto-oligosaccharides, glycol-oligosaccharides and mixtures thereof.

19. The method according to claim 1, wherein the composition further comprises effective amounts of lyophilisates of:
　i) *L. gasseri* 120.1 deposited by Medinova AG at Collection Nationale de Cultures de Microorganismes (CNCM) on Jun. 4, 2004 with accession number CNCM I-3218 and/or
　ii) *L. gasseri* 124.3 and/or *L. crispatus* 119.4 deposited by Medinova AG at Collection Nationale de Cultures de Microorganismes (CNCM) on Jul. 22, 2005 with accession number CNCM I-3484 and/or
　iii) *L. jensenii* KS 119.1 deposited by Medinova AG at Collection Nationale de Cultures de Microorganismes (CNCM) on Jun. 4, 2004 with accession number CNCM I-3217 for a total of 2 to 10 billion c.f.u. amounting to 50 to 200 mg.

20. The formulation according to claim 3, wherein the formulation further comprises effective amounts of lyophilisates of:
　i) *L. gasseri* 120.1 deposited by Medinova AG at Collection Nationale de Cultures de Microorganismes (CNCM) on Jun. 4, 2004 with accession number CNCM I-3218 and/or
　ii) *L. gasseri* 124.3 and/or *L. crispatus* 119.4 deposited by Medinova AG at Collection Nationale de Cultures de Microorganismes (CNCM) on Jul. 22, 2005 with accession number CNCM I-3484 and/or
　iii) *L. jensenii* KS 119.1 deposited by Medinova AG at Collection Nationale de Cultures de Microorganismes (CNCM) on Jun. 4, 2004 with accession number CNCM I-3217 for a total of 2 to 10 billion c.f.u. amounting to 50 to 200 mg.

21. A method for treating or preventing urogenital infections caused by pathogenic microorganisms in a female subject, comprising the following steps:
　(a) providing the formulation according to claim 3, and
　(b) administering the formulation in a therapeutically effective amount to the subject in need of treatment.

22. A prebiotic vaginal lubricant comprising:
　i) lactic acid: 50 mg;
　ii) citric acid: 30 mg;
　iii) glycerol: 80 mg;
　iv) carbomer: 5 mg;
　v) short-chain fructo-oligosaccharides: 50 mg;
　vi) thiosulfate: 10 mg;
　vii) glutamic acid: 10 mg; and
　viii) NaOH 0.1 M or HCl 0.1 M to pH 4.5 of the lubricant.

23. A method of treating or preventing bacterial vaginosis in a subject, comprising the following steps:
　(a) providing a vaginal capsule comprising:
　　i) lyophilisates of vaginal strains *L. gasseri* 120.1 deposited by Medinova AG at Collection Nationale de Cultures de Microorganismes (CNCM) on Jun. 4, 2004 with accession number CNCM I-3218 and *L. gasseri* 124.3 deposited by Medinova AG at Collection Nationale de Cultures de Microorganismes (CNCM) on Jun. 4, 2004 with accession number CNCM I-3220 at concentrations of 1011 c.f.u./g: 100 mg each;
　　ii) calcium-lactate pentahydrate: 60 mg;
　　iii) dibasic magnesium citrate: 30 mg;
　　iv) alanine: 40 mg;
　　v) arabinogalactan: 100 mg;
　　vi) dimethyl sulfone (MSM): 30 mg;
　　vii) excipients: 140 mg; and
　(b) administering the vaginal capsule to the subject in need of treatment.

\* \* \* \* \*